(12) United States Patent
Bi et al.

(10) Patent No.: US 8,426,414 B2
(45) Date of Patent: Apr. 23, 2013

(54) MODULATORS OF G PROTEIN-COUPLED RECEPTOR 88

(75) Inventors: Yingzhi Bi, Plainsboro, NJ (US); Carolyn Diane Dzierba, Middletown, CT (US); Joanne J. Bronson, Durham, CT (US); Cynthia Fink, Lebanon, NJ (US); Michael Green, Easton, PA (US); David Kimball, East Windsor, NJ (US); John E. Macor, Gullford, CT (US); Soojin Kwon, Haworth, NJ (US); Yulian Zhang, Yardley, PA (US); Greg Zipp, Robbinsville, NJ (US)

(73) Assignees: Bristol-Myers Squibb Company, Princeton, NJ (US); Lexicon Pharmaceuticals, Inc., The Woodlands, TX (US)

( * ) Notice: Subject to any disclaimer, the term of this patent is extended or adjusted under 35 U.S.C. 154(b) by 344 days.

(21) Appl. No.: 12/897,004

(22) Filed: Oct. 4, 2010

(65) Prior Publication Data
US 2011/0251204 A1 Oct. 13, 2011

Related U.S. Application Data

(60) Provisional application No. 61/250,091, filed on Oct. 9, 2009.

(51) Int. Cl.
*C07D 213/56* (2006.01)
*C07D 241/12* (2006.01)
*A61K 31/4418* (2006.01)
*A61K 31/4965* (2006.01)
*A61P 25/00* (2006.01)

(52) U.S. Cl.
USPC ......... 514/252.1; 514/277; 544/336; 546/336

(58) Field of Classification Search ................ None
See application file for complete search history.

(56) References Cited

FOREIGN PATENT DOCUMENTS

| | | |
|---|---|---|
| CN | 1733708 | 2/2006 |
| JP | 2007-217408 | 8/2007 |
| WO | WO 94/12461 | 6/1994 |
| WO | WO 96/21464 | 7/1996 |
| WO | WO 03/086325 | 10/2003 |
| WO | WO03/103666 A2 | 12/2003 |
| WO | WO2004/047738 A2 | 6/2004 |
| WO | WO 2004/056745 | 7/2004 |
| WO | WO 2004/072018 | 8/2004 |
| WO | WO 2005/000309 | 1/2005 |
| WO | WO2005/051890 A1 | 6/2005 |
| WO | WO 2006/012227 | 2/2006 |
| WO | WO2006/027252 A1 | 3/2006 |
| WO | WO 2007/117715 | 10/2007 |
| WO | WO2007/129188 A1 | 11/2007 |
| WO | WO 2008/022154 | 2/2008 |
| WO | WO 2011/044195 | 4/2011 |
| WO | WO 2011/044225 | 4/2011 |

OTHER PUBLICATIONS

Garrido, Dulce M., et al, "Synthesis and Activity of Small Molecule GPR40 Agonists," Bioorganic & Medicinal Chemistry Letters, vol. 16, No. 7, pp. 1840-1845, 2006.
U.S. Appl. No. 12/895,916, filed Oct. 1, 2010, Bi et al.
U.S. Appl. No. 12/898,016, filed Oct. 5, 2010, Dzierba et al.

*Primary Examiner* — Sreeni Padmanabhan
*Assistant Examiner* — Irina Neagu
(74) *Attorney, Agent, or Firm* — Pamela A. mingo; Gary D. Greenblatt

(57) ABSTRACT

The present disclosure is generally directed to compounds which can modulate G-protein coupled receptor 88, compositions comprising such compounds, and methods for modulating G-protein coupled receptor 88.

7 Claims, No Drawings

MODULATORS OF G PROTEIN-COUPLED RECEPTOR 88

CROSS-REFERENCE TO RELATED APPLICATIONS

This application claims the benefit of U.S. provisional application Ser. No. 61/250,091 filed Oct. 9, 2009.

The present disclosure is generally directed to compounds which can modulate G-protein coupled receptor 88, compositions comprising such compounds, and methods for modulating G-protein coupled receptor 88.

GPR88 is an orphan member of the G protein coupled receptor (GPCR) superfamily. GPR88 demonstrates GPCR activity several assays including GTPgS binding, calcium influx, and cAMP inhibition assays. The receptor exhibits high expression in the CNS, with measurable expression in peripheral tissues including liver. CNS expression is particularly robust in striatum, paralleling that of the dopamine D2 receptor (Mizushima et. al, *Genomics* 69, 314-321 (2000)) suggesting the receptor may play a role in regulating dopaminergic activity. Consistent with this, genetically-modified mice that lack GPR88 expression exhibit enhanced response to dopaminergic agonists, altered performance in models relevant to schizophrenia (prepulse inhibition, conditioned avoidance responding) and depression (forced swim test). These results demonstrate therapeutic potential for GPR88 in treating CNS diseases. Transcriptional profiling studies have also revealed GPR88 expression is altered by treatments or conditions related to bipolar disorder (Ogden et al., *Mol Psychiatry* 2004 November; 9(11):1007-29 and Brandish, et al. *Neuron*, Vol. 45, 861-872, Mar. 24, 2005, schizophrenia (Matsuoka, et al. *Synapse* 2008 January; 62(1):1-7), and depression (Conti et al., *Mol. Psychiatry.* 2007 February; 12(2):167-89.), providing additional support for GPR88 as an essential modulator of CNS signaling pathways related to psychiatric disease.

GPR88 is also expressed liver tissue suggesting GPR88 signaling may contribute to regulation of metabolic processes. Initial phenotypic characterization of genetically-modified mice lacking GPR88 expression (Level 1 data) suggests these animals exhibit altered response to glucose, insulin levels and triglycerides. These results suggest compounds that modulate GPR88 activity may have utility in metabolic diseases.

Based on these data, compounds that modulate GPR88 activity (agonists, antagonists, or modulators) are predicted to have therapeutic utility in the treatment of psychosis, cognitive deficits in schizophrenia, affective disorders, attention deficit hyperactivity disorders, bipolar disorder, drug addiction, Parkinson's disease, Alzheimer's disease, obesity and diabetes.

In a first aspect the present disclosure provides a compound of Formula (I)

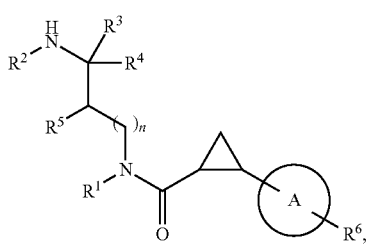

(I)

or a pharmaceutically acceptable salt thereof, wherein
n is 0 or 1;
A is selected from imidazolyl; phenyl; pyrazinyl; pyrimidinyl; pyridinyl; and thiazolyl;
$R^1$ is selected from:

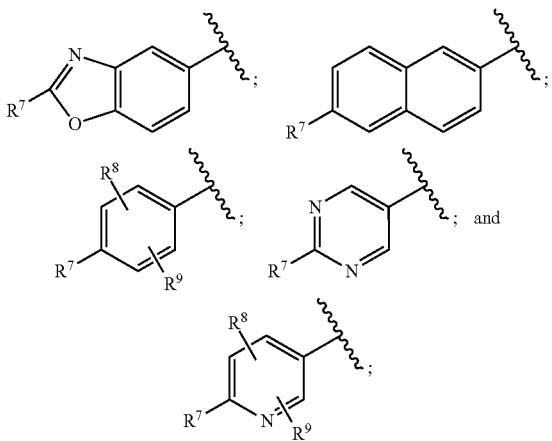

wherein "⌇" denotes the point of attachment to the parent molecular moiety;

$R^2$ is selected from hydrogen; $C_1$-$C_3$ alkyl; $C_3$-$C_6$ cycloalkyl; and $C_3$-$C_6$ cycloalkyl-$C_1$-$C_3$ alkyl;

$R^3$ is selected from hydrogen; $C_1$-$C_6$ alkyl; $C_1$-$C_3$ alkoxy-$C_1$-$C_3$ alkyl; hydroxy-$C_1$-$C_3$ alkyl;

or, $R^2$ and $R^3$, together with the atoms to which they are attached, form a pyrrolidine ring;

$R^4$ is selected from hydrogen; $C_1$-$C_3$ alkyl; and hydroxy-$C_1$-$C_3$ alkyl; or $R^3$ and $R^4$, together with the carbon atom to which they are attached, form a carbonyl group, or form a ring selected from $C_3$-$C_6$ cycloalkyl; tetrahydrofuryl; and tetrahydropyranyl;

$R^5$ is selected from hydrogen and $C_1$-$C_3$ alkyl; or $R^4$ and $R^5$, together with the carbon atoms to which they are attached, form a cyclopentyl or cyclohexyl ring;

$R^6$ is selected from hydrogen; $C_1$-$C_3$ alkoxy; $C_1$-$C_3$ alkyl; and halo; and $R^7$ is selected from
$C_3$-$C_6$ alkenyl;
$C_2$-$C_6$ alkenyloxy;
$C_3$-$C_6$ alkoxy;
$C_1$-$C_3$ alkoxy-$C_2$-$C_3$ alkynyl;
$C_1$-$C_6$ alkyl;
$C_2$-$C_6$ alkynyl;
$C_5$-$C_6$ cycloalkenyl;
$C_3$-$C_6$ cycloalkyl optionally substituted with one or two $C_1$-$C_3$ alkyl groups;
$C_3$-$C_6$ cycloalkyl-$C_1$-$C_3$ alkoxy, wherein the cycloalkyl is optionally substituted with one or two $C_1$-$C_3$ alkyl groups;
$C_3$-$C_7$ cycloalkyloxy optionally substituted with one or two $C_1$-$C_3$ alkyl groups;
halo;
heterocyclyl optionally substituted with one or two groups independently selected from $C_1$-$C_3$ alkyl, halo-$C_1$-$C_3$ alkyl, and phenyl;
heterocyclyloxy optionally substituted with one or two halo-$C_1$-$C_3$ alkyl groups;
phenoxy-$C_1$-$C_3$ alkoxy;
phenyl optionally substituted with one, two, or three substituents independently selected from $C_1$-$C_3$ alkoxy, $C_1$-$C_6$ alkoxy-$C_1$-$C_3$ alkyl, $C_1$-$C_3$ alkoxycarbonyl, $C_1$-$C_3$ alkoxycarbonyl-$C_1$-$C_3$ alkyl, $C_1$-$C_6$ alkyl, $C_1$-$C_3$ alkylsulfanyl, $C_2$-$C_6$ alkynyl, cyano-$C_1$-$C_3$ alkyl, halo, halo-$C_1$-$C_3$ alkoxy, —$NH_2$, and phenoxy optionally substituted with one or two groups independently selected from $C_1$-$C_3$ alkoxy-$C_1$-$C_3$ alkyl and halo; provided that when the phenyl is substituted the first substituent is in the para position on the phenyl ring;

phenyl-$C_1$-$C_3$ alkoxy, wherein the phenyl is optionally substituted with one or two groups independently selected from $C_1$-$C_3$ alkoxy-$C_1$-$C_3$ alkyl and halo; and X—C(O)—NH—; wherein X is selected from $C_1$-$C_3$ alkoxy; $C_1$-$C_6$ alkyl; $C_3$-$C_{10}$ cycloalkyl; and heterocyclyl optionally substituted with $C_1$-$C_6$ alkyl;

$R^8$ is selected from hydrogen; $C_1$-$C_3$ alkyl; and halo; and $R^9$ is selected from hydrogen; $C_1$-$C_3$ alkyl; and halo.

In a first embodiment of the first aspect the present disclosure provides a compound of Formula (I), or a pharmaceutically acceptable salt thereof, wherein B is phenyl.

In a second embodiment of the first aspect the present disclosure provides a compound of Formula (I), or a pharmaceutically acceptable salt thereof, wherein B is pyridinyl.

In a third embodiment of the first aspect the present disclosure provides a compound of Formula (I), or a pharmaceutically acceptable salt thereof, wherein B is selected from imidazolyl; pyrazinyl; pyrimidinyl; and thiazolyl.

In a second aspect the present disclosure provides a compound of formula (II)

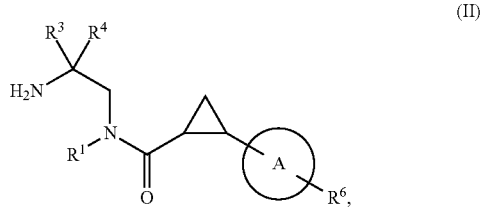

or a pharmaceutically acceptable salt thereof, wherein
A is selected from pyrazinyl and pyridinyl;
$R^1$ is selected from:

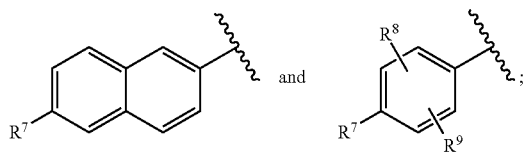

wherein "⁓" denotes the point of attachment to the parent molecular moiety;
$R^3$ is selected from $C_4$ alkyl and $C_1$ alkoxy-$C_2$ alkyl;
$R^4$ is hydrogen; or
$R^3$ and $R^4$, together with the carbon atom to which they are attached, form a carbonyl group, or form a ring selected from $C_5$ cycloalkyl and tetrahydropyranyl;
$R^6$ is selected from hydrogen and halo; and
$R^7$ is selected from
$C_5$ alkynyl;
$C_3$ cycloalkyl;
$C_4$ cycloalkyl-$C_1$ alkoxy; and
phenyl optionally substituted with one substituent selected from $C_3$ alkoxy, $C_1$ alkoxy-$C_1$ alkyl, $C_3$ alkyl, and $C_2$ alkynyl, provided that when the phenyl is substituted the substituent is in the para position on the phenyl ring;

In a third aspect the present disclosure provides a composition comprising a compound of Formula (I), or a pharmaceutically acceptable salt thereof, and a pharmaceutically acceptable carrier.

In a fourth aspect the present disclosure provides a method of treating a disorder selected from a neurological disorder or a metabolic disease in a mammal, comprising administering to the mammal a therapeutically effective amount of a compound of Formula (I), or a pharmaceutically acceptable salt thereof.

In a first embodiment of the fourth aspect the mammal is a human.

In a second embodiment of the fourth aspect the disorder is a neurological disorder is selected from psychosis, cognitive deficits in schizophrenia, affective disorders, attention deficit hyperactivity disorders, drug addiction, Parkinson's disease, and Alzheimer's disease.

In a third embodiment of the fourth aspect the disorder is a metabolic disease selected from obesity and diabetes.

In a fifth aspect the present disclosure provides a method of modulating G protein-coupled receptor 88 in a mammal, comprising administering to the mammal a therapeutically effective amount of a compound of Formula (I), or a pharmaceutically acceptable salt thereof.

In a first embodiment of the fifth aspect the mammal is a human.

In a second embodiment of the fifth aspect the G protein-coupled receptor 88 is modulated in order to treat a neurological disorder or metabolic disease.

In a third embodiment of the fifth aspect the G protein-coupled receptor 88 is modulated in order to treat a neurological disorder wherein the neurological disorder is selected from psychosis, cognitive deficits in schizophrenia, affective disorders, attention deficit hyperactivity disorders, bipolar disorder, drug addiction, Parkinson's disease, and Alzheimer's disease.

In a fourth embodiment of the fifth aspect the G protein-coupled receptor 88 is modulated in order to treat a metabolic disease wherein the metabolic disease is selected from obesity and diabetes.

Other embodiments of the present disclosure may comprise suitable combinations of two or more of embodiments and/or aspects disclosed herein.

Yet other embodiments and aspects of the disclosure will be apparent according to the description provided below.

The description of the present disclosure herein should be construed in congruity with the laws and principals of chemical bonding. In some instances it may be necessary to remove a hydrogen atom in order accommodate a substituent at any given location.

It should be understood that the compounds encompassed by the present disclosure are those that are suitably stable for use as pharmaceutical agent.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

In some instances, the number of carbon atoms in any particular group is denoted before the recitation of the group. For example, the term "$C_{2-6}$ alkenyl" denotes an alkenyl group containing two to six carbon atoms. Where these designations exist they supercede all other definitions contained herein.

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkynyl," as used herein, refers to an alkynyl group substituted with one, two, or three alkoxy groups.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to six carbon atoms.

The term "alkylsulfanyl," as used herein, refers to an alkyl group attached to the parent molecular moiety through a sulfur atom.

The term "alkynyl," as used herein, refers to a straight or branched chain group of two to six carbon atoms containing at least one carbon-carbon triple bond.

The term "carbonyl," as used herein, refers to —C(O)—.

The term "cyano," as used herein, refers to —CN.

The term "cyanoalkyl," as used herein, refers to an alkyl group substituted with one, two, or three cyano groups.

The term "cycloalkenyl," as used herein, refers to a partially unsaturated monocyclic, hydrocarbon ring system having five to seven carbon atoms and zero heteroatoms. Representative examples of cycloalkenyl groups include, but are not limited to, cyclopentenyl, cyclohexenyl, and cycloheptenyl.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl.

The term "(cycloalkyl)alkoxy," as used herein, refers to a cycloalkyl group attached to the parent molecular moiety through an alkoxy group.

The term "cycloalkyloxy," as used herein, refers to a cycloalkyl group attached to the parent molecular moiety through an oxygen atom.

The term "(cycloalkyl)alkyl," as used herein, refers to an alkyl group substituted with one, two, or three cycloalkyl groups.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, thiomorpholinyl, 7-azabicyclo[2.2.1]hept-7-yl, 2-azabicyclo[2.2.2]oc-2-tyl, and 2-azabicyclo[2.2.2]oc-3-tyl.

The term "heterocyclyloxy," as used herein, refers to a heterocyclyl group attached to the parent molecular moiety through an oxygen atom.

The term "hydroxy," as used herein, refers to —OH.

The term "hydroxyalkyl," as used herein, refers to an alkyl group substituted with one, two, or three hydroxy groups.

The term "phenoxy," as used herein, refers to a phenyl group attached to the parent molecular moiety through an oxygen atom.

The term "phenylalkoxy," as used herein, refers to a phenyl group attached to the parent molecular moiety through an alkoxy group.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to modulate G protein-coupled receptor 88. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of Formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of Formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: HATU for O-(7-azabenzotriazol-1-yl)-N,N,N',N'-tetramethyluronium hexafluorophosphate; BOP for benzotriazol-1-yloxytris(dimethylamino)phosphonium hexafluorophosphate; EDC or EDCI for 1-(3-dimethylaminopropyl)-3-ethylcarbodiimide hydrochloride; TBTU for O-benzotriazol-1-yl-N,N,N',N'-tetramethyluronium tetrafluoroborate; BOC or Boc for tert-butoxycarbonyl; Ar for aryl; Et for ethyl; tBu for tert-butyl; Ph for phenyl; Me for methyl; DMSO for dimethylsulfoxide; h or hr or hrs for hours; DMF for N,N-dimethylformamide; min or mins for minutes; DCM for dichloromethane; TEA or Et$_3$N for triethylamine; EtOAc for ethyl acetate; Hex or hex for hexanes; MeCN for acetonitrile; TFA for trifluoroacetic acid; RT or rt or r.t. for retention time or room temperature; TBS for tert-butyldimethylsilyl; TBAF for tetrabutylammonium fluoride; DIEA for diisopropylethylamine; Et$_2$O for diethyl ether; Py.SO$_3$ for pyridine 2-sulfonate; DCE for 1,2-dichloroethane; and MeOD for CD$_3$OD.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of formula 8 are prepared by the methods outlined in Scheme 1. The hydroxyl group of a compound of formula 1 is oxidized with an appropriate oxidizing reagent such as sulfur trioxide pyridine complex to provide aldehyde 2. Reductive amination of compound 2 with 4-bromoaniline 3 affords intermediate 4. Intermediate 4 is then coupled with a carboxylic acid, such as compound 5, via its corresponding acyl chloride or using standard peptide coupling reagents such as HATU, BOP, EDC, TBTU, in the presence of a base, such as N,N-diisopropylethylamine, and a solvent, to produce 6. Suzuki coupling or other catalytic cross coupling of 6 with an appropriate coupling reagent gives compound 7. Removal of the t-butyl carbamate protecting group under acidic conditions affords compounds of formula 8.

Scheme 1

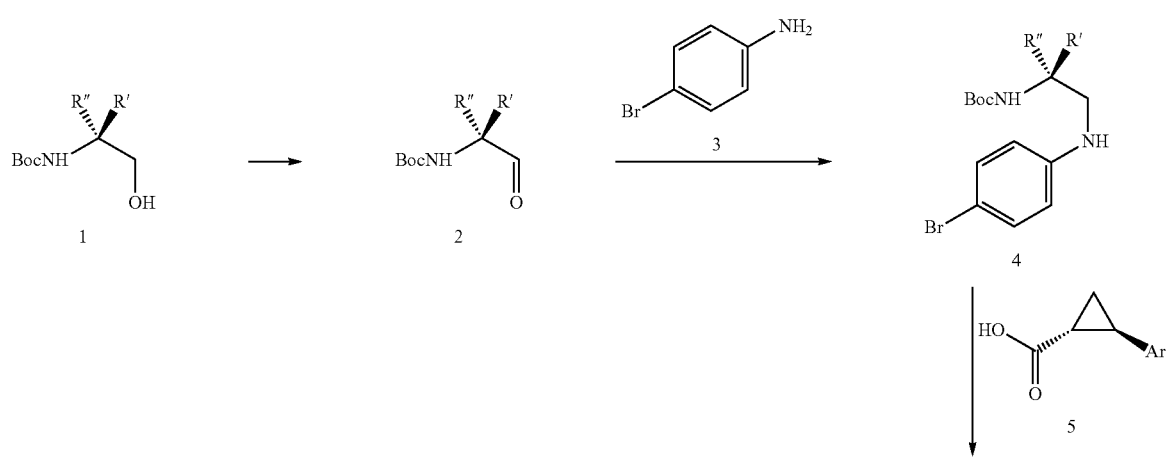

13

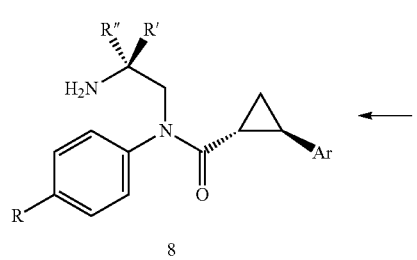

8

-continued

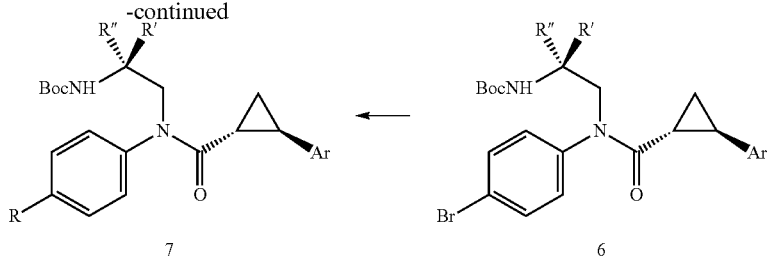

7        6

14

Compounds of formula 1 that are not commercially available are prepared by reduction of the corresponding acids as shown in Scheme 2.

Scheme 2

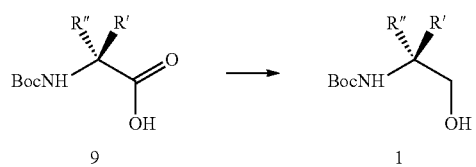

9        1

The aryl cyclopropanecarboxylic acid 5 that are not commercially available are prepared according to Scheme 3. The aryl alkene 10 is reacted with t-butyldiazoacetate 11 under catalytic conditions to give aryl cyclopropanecarboxylic acid t-butyl ester 12. Alternatively, epoxidation of compound 10 afford epoxide 13. Cyclopropanation of compound 13 with t-butyl diethylphosphonoacetate 14 provides aryl cyclopropanecarboxylic acid t-butyl ester 12. The t-butyl is removed under acidic conditions to afford the aryl cyclopropanecarboxylic acid 5.

Scheme 3

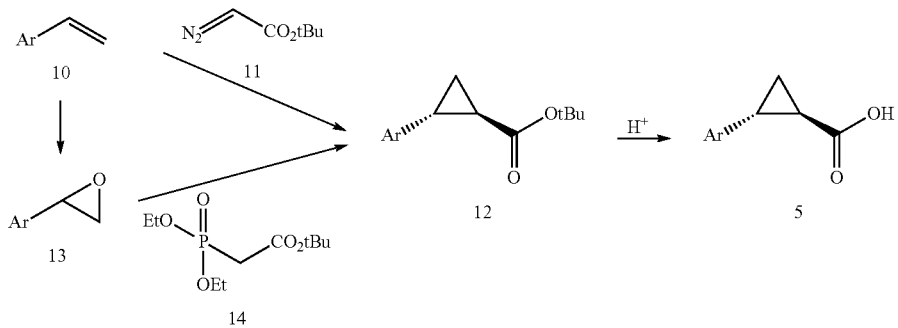

The aryl cyclopropanecarboxylic acid t-butyl ester 12 is also prepared from aryl aldehyde 15 as outlined in Scheme 4. Reaction of aryl aldehyde 15 with t-butyl triphenylphosphinoacetate 16 gives compound 17. cyclopropanation of 17 provides the aryl cyclopropanecarboxylic acid t-butyl ester 12.

Scheme 4

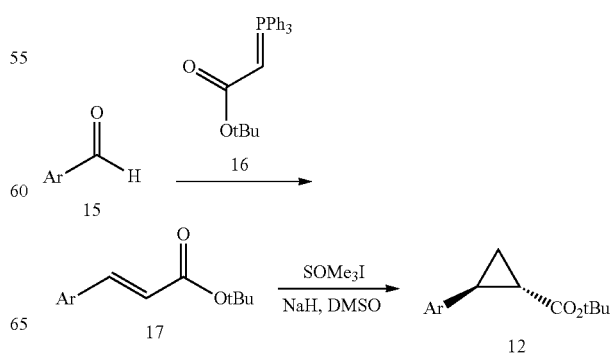

Compounds of formula 25 are prepared by the methods outlined in Scheme 5. The phenol group in 4-aminophenol 18 is protected as a silyl ether to give compound 19. Reductive amination of compound 19 with an aldehyde such as 2 affords intermediate 21. Intermediate 21 is then coupled with a carboxylic acid, such as compound 5, via its corresponding acyl chloride or using standard peptide coupling reagents such as HATU, BOP, EDC, TBTU, in the presence of a base, such as N,N-diisopropylethylamine, and a solvent, to produce 22. The phenol protecting group of compound 22 is removed to provide the phenol compound 23. Alkylation of compound 23 with an appropriate alkylating agent under basic conditions affords compounds of formula 24. Removal of the t-butyl carbamate protecting group under acidic conditions affords compounds of formula 25.

Scheme 5

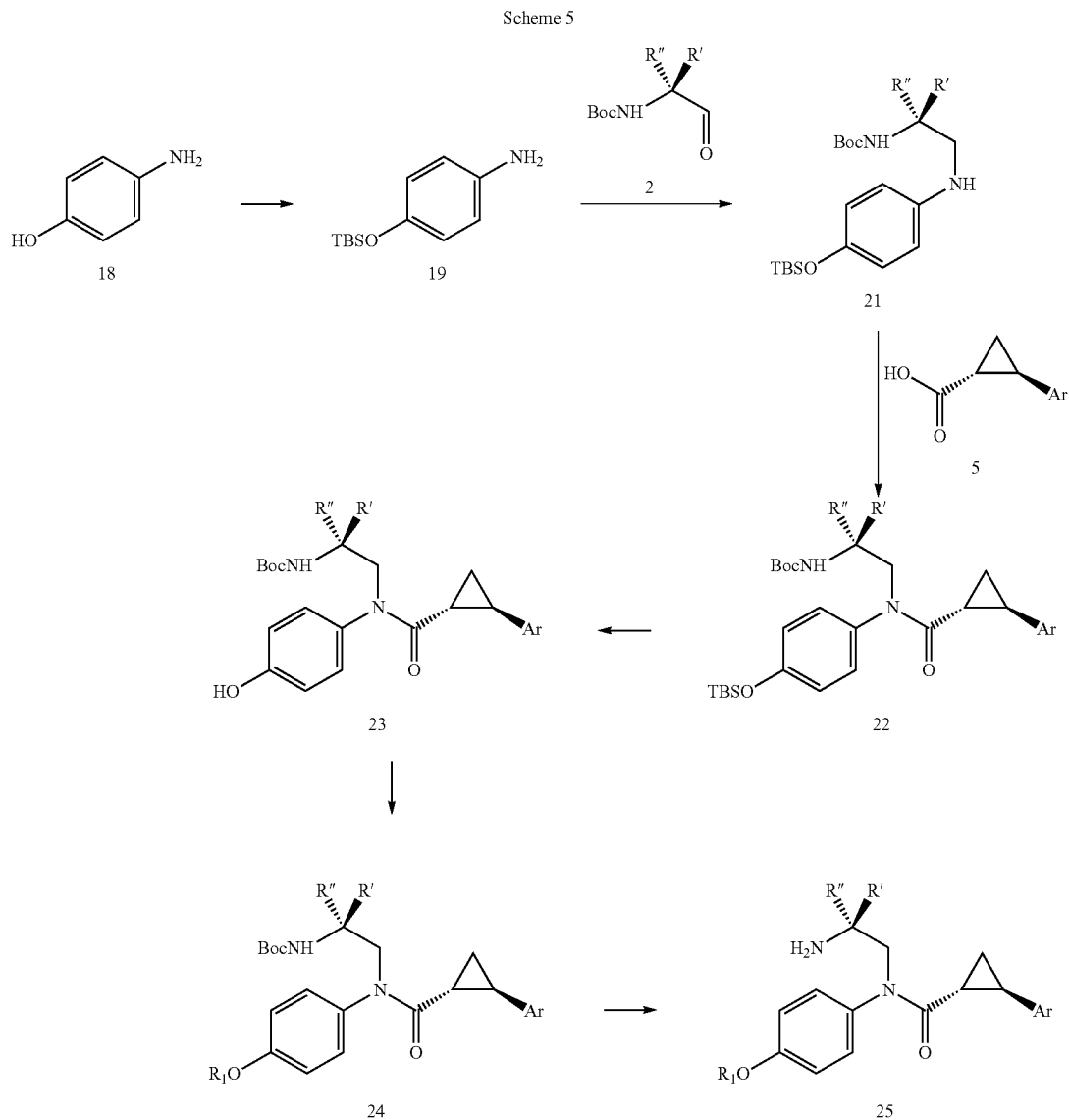

Compounds of formula 30 are prepared by the methods outlined in Scheme 6. Reductive amination of compound 26 with an aldehyde such as 2 affords intermediate 27. Intermediate 27 is then coupled with a carboxylic acid, such as compound 5, via its corresponding acyl chloride or using standard peptide coupling reagents such as HATU, BOP, EDC, TBTU, in the presence of a base, such as N,N-diisopropylethylamine, and a solvent, to produce 28. Suzuki coupling or other catalytic cross coupling of 28 with an appropriate coupling reagent gives compound 29. Removal of the t-butyl carbamate protecting group under acidic conditions affords compounds of formula 30.

Scheme 6

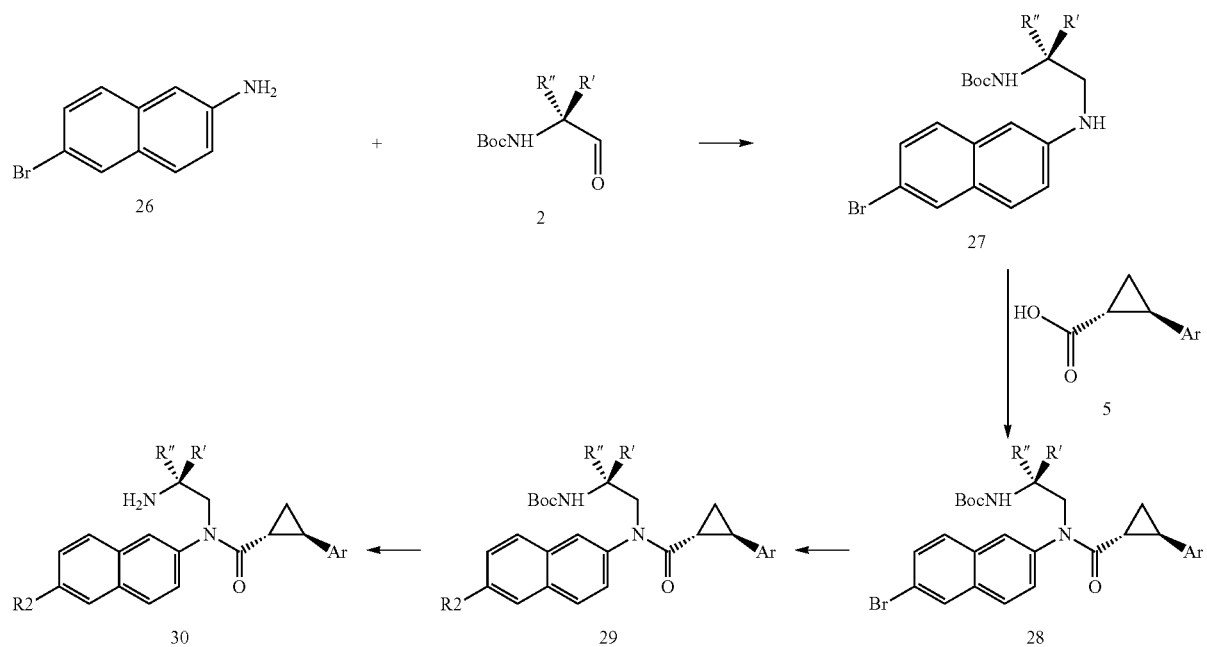

Various analogs synthesized using Schemes 1-6 are listed in Table 1 or the structure is shown following the table.

TABLE 1

(Ia)

| Example | B | R | R' | R'' | Ar | (M + H)+ |
|---|---|---|---|---|---|---|
| 1 | Ph | 4-methoxymethylphenyl | sec-butyl | H | pyridin-2-yl | 458.1 |
| 2 | Ph | 4-isopropoxyphenyl | sec-butyl | H | pyridin-2-yl | 472.3 |
| 3 | Ph | 4-propylphenyl | sec-butyl | H | pyridin-2-yl | 456.3 |
| 4 | Ph | 4-methoxymethylphenyl | sec-butyl | H | 5-fluoro-pyridin-2-yl | 476.2 |
| 5 | Ph | 4-propynylphenyl | sec-butyl | H | pyridin-2-yl | 452.2 |
| 6 | Ph | 4-propylphenyl | $(CH_2)_4$ | | 6-fluoro-pyridin-2-yl | 472.2 |
| 7 | Ph | 4-isopropoxyphenyl | $(CH_2)_4$ | | 6-fluoro-pyridin-2-yl | 488.2 |
| 8 | Ph | 4-methoxymethylphenyl | $(CH_2)_4$ | | 6-fluoro-pyridin-2-yl | 474.2 |
| 9 | Ph | 4-propylphenyl | $(CH_2)_2O(CH_2)_2$ | | pyridin-2-yl | 470.3 |
| 10 | Ph | 4-propylphenyl | sec-butyl | H | 3-fluoro-pyridin-2-yl | 474.3 |
| 11 | Ph | 4-propylphenyl | sec-butyl | H | pyrazin-2-yl | 457.3 |
| 12 | Ph | cyclobutylmethoxy | sec-butyl | H | 5-fluoro-pyridine-2-yl | 440.2 |
| 13 | Ph | cyclobutylmethoxy | sec-butyl | H | pyridin-2-yl | 422.3 |
| 14 | Ph | 4-propylphenyl | sec-butyl | H | 6-fluoro-pyridin-2-yl | 474.3 |
| 15 | Ph | 4-isopropoxyphenyl | sec-butyl | H | 6-fluoro-pyridin-2-yl | 490.3 |
| 16 | Ph | 4-methoxymethylphenyl | sec-butyl | H | 6-fluoro-pyridin-2-yl | 476.3 |
| 17 | Ph | cyclobutylmethoxy | sec-butyl | H | 5-fluoro-pyridine-2-yl | 440.3 |

TABLE 1-continued (Ia)

| Example | B | R | R' | R" | Ar | (M + H)⁺ |
|---|---|---|---|---|---|---|
| 18 | Ph | 4-propylphenyl | 1-methoxy ethyl | H | pyrazin-2-yl | 459.3 |
| 19 | Ph | pent-1-ynyl | sec-butyl | H | 6-fluoro-pyridin-2-yl | 422.3 |
| 20 | Naphthyl | cyclopropyl | sec-butyl | H | 6-fluoro-pyridin-2-yl | 446.2 |

EXAMPLES

In the following examples, all temperatures are given in degrees Centigrade. Melting points were recorded on a Meltemp 3.0 Laboratory Devices, Inc. capillary melting point apparatus and are uncorrected. Proton magnetic resonance ($^1$H NMR) spectra were recorded on a Bruker Avance 300, a Bruker Avance 400, or a Bruker Avance 500 spectrometer. All spectra were determined in the solvents indicated and chemical shifts are reported in δ units downfield from the internal standard tetramethylsilane (TMS) and interproton coupling constants are reported in Hertz (Hz). Multiplicity patterns are designated as follows: s, singlet; d, doublet; t, triplet; q, quartet; m, multiplet; br, broad peak; dd, doublet of doublet; br d, broad doublet; dt, doublet of triplet; br s, broad singlet; dq, doublet of quartet Infrared (IR) spectra using potassium bromide (KBr) or sodium chloride film were determined on a Jasco FT/IR-410 or a Perkin Elmer 2000 FT-IR spectrometer from 4000 cm$^{-1}$ to 400 cm$^{-1}$, calibrated to 1601 cm$^{-1}$ absorption of a polystyrene film and reported in reciprocal centimeters (cm$^{-1}$). Optical rotations $[\alpha]_D$ were determined on a Rudolph Scientific Autopol IV polarimeter in the solvents indicated; concentrations are given in mg/mL. Low resolution mass spectra (MS) and the apparent molecular (MH⁺) or (M−H)⁺ was determined on a Finnegan SSQ7000. High resolution mass spectra were determined on a Finnegan MAT900. Liquid chromatography (LC)/mass spectra were run on a Shimadzu LC coupled to a Water Micromass ZQ.

Example 1

(1R,2R)-2-Pyridin-2-yl-cyclopropanecarboxylic acid ((2S,3S)-2-amino-3-methyl-pentyl)-(4'-methoxymethyl-biphenyl-4-yl)-amide

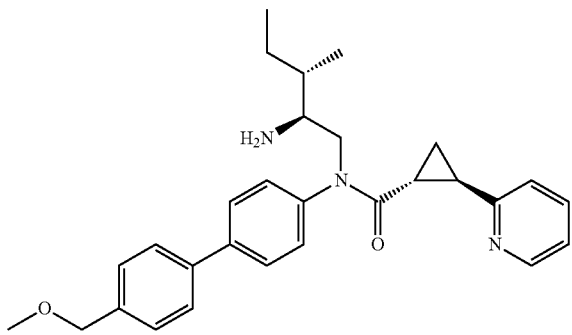 [SMILES: CC[C@H](C)[C@H](N)CN(C(=O)[C@@H]1C[C@H]1c1ccccn1)c1ccc(-c2ccc(COC)cc2)cc1]

Part A.
(1R,2R)-2-Pyridin-2-yl-cyclopropanecarboxylic acid

A solution of 2-vinyl pyridine (0.29 mL, 2.7 mmol), 5,10,15,20-tetraphenyl-21H,23H-porphine cobalt(II) (36 mg, 0.054 mmol), tert-butyl diazoacetate (0.45 mL, 3.2 mmol) and toluene (12 mL) was heated in a sealed vessel at 80° C. for 2 h. The deep purple reaction mixture was cooled to room temperature and then concentrated. The residue was purified by column chromatography on silica gel (10% ethyl acetate in hexanes) to afford a clear, colorless oil that was dissolved in dichloromethane (20 mL) and treated with 4 N HCl in dioxane (5 mL). The resulting reaction was maintained at room temperature overnight, then concentrated to afford 480 mg (89%) of a solid that was purified by chiral chromatography (ChiralPak AD-H 20×250 mm eluting 16% ethanol in hexanes at 5 mL/min) to afford (1R,2R)-2-pyridin-2-yl-cyclopropanecarboxylic acid as a tan solid: $^1$H NMR (400 MHz, C$_6$D$_6$) δ 8.38 (d, J=4.8 Hz, 1H), 6.99 (td, J=7.7, 1.8 Hz, 1H), 6.78 (d, J=7.8 Hz, 1H), 6.60 (ddd, J=7.5, 4.9, 1.0 Hz, 1H), 2.74 (dddd, J=16.5, 8.8, 5.6, 3.8 Hz, 2H), 1.83 (ddd, J=8.7, 5.7, 3.3 Hz, 1H), 1.76 (ddd, J=8.7, 5.5, 3.3 Hz, 1H), 1.49 (s, 9H); LRMS (ESI) m/e 164.1 [(M+H)⁺, calcd for C$_9$H$_{10}$NO$_2$ 164.1].

Part B. [(R)-3-(4-Bromo-phenyl)-1-((S)-sec-butyl)-4-oxo-4-((1R,2R)-2-pyridin-2-yl-cyclopropyl)-butyl]-carbamic acid tert-butyl ester A solution of (1R,2R)-2-pyridin-2-yl-cyclopropanecarboxylic acid (400 mg, 2.0 mmol) and dichloromethane (20 mL) was treated with oxalyl chloride (0.35 mL, 4.0 mmol) and DMF (50 μL). The resulting reaction mixture was maintained at 35° C. for 2 h, then allowed to cool to room temperature and concentrated to dryness. The residue was dissolved in dichloromethane (20 mL) and treated with {(1S,2S)-1-[(4-bromo-phenylamino)-methyl]-2-methylbutyl}-carbamic acid tert-butyl ester (0.74 g, 2.0 mmol) and triethylamine (1.1 mL, 8.0 mmol), and the resulting reaction mixture was maintained at room temperature overnight. The resulting suspension was partitioned between ethyl acetate (100 mL) and saturated aqueous sodium bicarbonate (100 mL). The layers were separated, and the aqueous layer was extracted with ethyl acetate (100 mL). Combined organic layers were washed with brine (100 mL), dried (MgSO$_4$), filtered and concentrated to afford a residue that was purified by column chromatography on silica gel (25% ethyl acetate in hexanes) to afford [(R)-3-(4-bromo-phenyl)-1-((S)-sec-butyl)-4-oxo-4-((1R,2R)-2-pyridin-2-yl-cyclopropyl)-butyl]-carbamic acid tert-butyl ester (720 mg, 70% yield) as a clear, colorless oil: $^1$H NMR (400 MHz, CDCl$_3$) δ 8.32 (d, J=4.3 Hz, 1H), 7.54 (td, J=7.6, 1.5 Hz, 1H), 7.48 (d, J=8.1 Hz, 2H), 7.20 (d, J=7.8 Hz, 1H), 7.15 (d, J=7.8 Hz, 2H), 7.04 (dd, J=6.9, 5.2 Hz, 1H), 4.97 (d, J=9.3 Hz, 1H), 4.37 (dd, J=13.4, 12.1 Hz, 1H), 3.67-3.80 (m, 1H), 3.14 (dd, J=13.9, 3.8 Hz, 1H), 2.69 (ddd, J=9.0, 5.6, 4.0 Hz, 1H), 1.87-1.96 (m, 1H), 1.55-1.65 (m, 1H), 1.47 (s, 11H), 1.06-1.16 (m, 1H), 0.83-0.93 (m, 6H); LRMS (ESI) m/e 516.0 [(M+H)$^+$, calcd for C$_{26}$H$_{35}$BrN$_3$O$_3$ 516.2].

Part C. ((1S,2S)-1-{[(4'-Methoxymethyl-biphenyl-4-yl)-(2-pyridin-2-yl-cyclopropanecarbonyl)-amino]-methyl}-2-methyl-butyl)-carbamic acid tert-butyl ester A mixture of [(R)-3-(4-bromophenyl)-1-((S)-sec-butyl)-4-oxo-4-((1R,2R)-2-pyridin-2-yl-cyclopropyl)-butyl]-carbamic acid tert-butyl ester (32 mg, 0.062 mmol), 4-methoxymethyl phenylboronic acid (15 mg, 0.093 mmol), dichloro[1,1'-bis(diphenylphosphino)ferrocene]palladium (II) dichloromethane adduct (5 mg, 0.0062 mmol), potassium phosphate (40 mg, 0.19 mmol), dimethoxyethane (1.5 mL) and water (0.5 mL) was heated in a sealed vessel by microwave irradiation at 160° C. for 5 min. The resulting mixture was poured into 1 N aqueous sodium hydroxide solution (10 mL) and extracted with dichloromethane (3×10 mL). Combined organics were dried (MgSO$_4$), filtered and concentrated under reduced pressure to afford a residue that was purified by preparative HPLC (neutral mobile phase) to afford ((1S,2S)-1-{[(4'-methoxymethyl-biphenyl-4-yl)-(2-pyridin-2-yl-cyclopropanecarbonyl)-amino]-methyl}-2-methyl-butyl)-carbamic acid tert-butyl ester (25 mg, 72% yield) as a colorless oil: $^1$H NMR (400 MHz, CDCl$_3$) δ 8.27-8.32 (m, 1H), 7.50-7.60 (m, 5H), 7.43 (d, J=8.1 Hz, 2H), 7.31 (d, J=7.8 Hz, 2H), 7.22 (d, J=7.1 Hz, 1H), 6.97-7.08 (m, 1H), 5.04-5.13 (m, 1H), 4.53 (s, 2H), 4.37-4.49 (m, 1H), 3.75-3.86 (m, 1H), 3.45 (s, 3H), 3.15-3.26 (m, 1H), 2.67-2.78 (m, 1H), 1.98-2.06 (m, 1H), 1.61 (br. s., 2H), 1.51-1.56 (m, 1H), 1.49 (s, 7H), 1.45 (br. s., 1H), 1.06-1.18 (m, 1H), 0.84-0.94 (m, 7H); LRMS (ESI) m/e 558.3 [(M+H)$^+$, calcd for C$_{34}$H$_{44}$N$_3$O$_4$ 558.3].

Part D. (1R,2R)-2-Pyridin-2-yl-cyclopropanecarboxylic acid ((2S,3S)-2-amino-3-methyl-pentyl)-(4'-methoxymethyl-biphenyl-4-yl)-amide A solution of ((1S,2S)-1-{[(4'-methoxymethyl-biphenyl-4-yl)-(2-pyridin-2-yl-cyclopropanecarbonyl)-amino]-methyl}-2-methyl-butyl)-carbamic acid tert-butyl ester (25 mg, 0.045 mmol) and dichloromethane (4 mL) was treated with a solution of HCl in dioxane (4 N, 0.5 mL) and the resulting reaction mixture was maintained at room temperature for 12 h. The reaction was then concentrated to dryness to afford (1R,2R)-2-pyridin-2-yl-cyclopropanecarboxylic acid ((2S,3S)-2-amino-3-methyl-pentyl)-(4'-methoxymethyl-biphenyl-4-yl)-amide (18 mg, 95% yield) as a white solid: $^1$H NMR (400 MHz, MeOD) δ 8.49 (d, J=5.8 Hz, 1H), 8.23 (t, J=7.8 Hz, 1H), 7.61-7.71 (m, 3H), 7.44-7.54 (m, 5H), 7.34 (d, J=8.1 Hz, 2H), 4.40 (s, 2H), 4.22 (dd, J=14.9, 9.1 Hz, 1H), 3.70 (dd, J=14.9, 2.5 Hz, 1H), 3.62-3.66 (m, 1H), 3.54-3.59 (m, 1H), 3.46-3.50 (m, 1H), 3.31 (s, 3H), 2.83-2.90 (m, 1H), 2.07-2.13 (m, 1H), 1.84-1.92 (m, 1H), 1.64-1.74 (m, 1H), 1.60 (dt, J=8.7, 5.5 Hz, 1H), 1.24-1.36 (m, 1H), 1.06-1.22 (m, 1H), 0.88 (d, J=6.8 Hz, 3H), 0.76 (t, J=7.3 Hz, 3H); LRMS (ESI) m/e 458.1 [(M+H)$^+$, calcd for C$_{29}$H$_{36}$N$_3$O$_2$ 458.3].

Example 2

(1R,2R)-2-Pyridin-2-yl-cyclopropanecarboxylic acid ((2S,3S)-2-amino-3-methyl-pentyl)-(4'-isopropoxy-biphenyl-4-yl)-amide

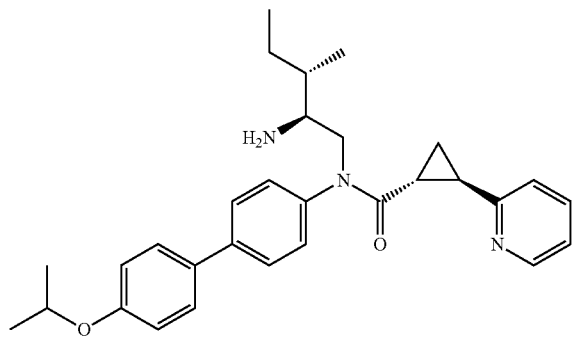 [SMILES: CC[C@H](C)[C@H](N)CN(C(=O)[C@@H]1C[C@H]1c1ccccn1)c1ccc(-c2ccc(OC(C)C)cc2)cc1]

Part A. ((1S,2S)-1-{[(4'-Isopropoxy-biphenyl-4-yl)-((1R,2R)-2-pyridin-2-yl-cyclopropanecarbonyl)-amino]-methyl}-2-methyl-butyl)-carbamic acid tert-butyl ester A mixture of [(R)-3-(4-bromo-phenyl)-1-((S)-sec-butyl)-4-oxo-4-((1R,2R)-2-pyridin-2-yl-cyclopropyl)-butyl]-carbamic acid tert-butyl ester (68 mg, 0.13 mmol), 4-isopropoxy phenylboronic acid (36 mg, 0.20 mmol), dichloro[1,1'-bis(diphenylphosphino)ferrocene]palladium (II) dichloromethane adduct (10 mg, 0.013 mmol), potassium phosphate (83 mg, 0.39 mmol), dimethoxyethane (1.5 mL) and water (0.5 mL) was heated in a sealed vessel by microwave irradiation at 160° C. for 5 min. The resulting mixture was poured into 1 N aqueous sodium hydroxide solution (15 mL) and extracted with dichloromethane (3×15 mL). Combined organics were dried (MgSO$_4$), filtered and concentrated under reduced pressure to afford a residue that was purified by preparative HPLC (neutral mobile phase) to afford ((1S,2S)-1-{[(4'-isopropoxy-biphenyl-4-yl)-((1R,2R)-2-pyridin-2-yl-cyclopropanecarbonyl)-amino]-methyl}-2-methyl-butyl)-carbamic acid tert-butyl ester (48 mg, 65% yield) as a colorless oil: $^1$H NMR (400 MHz, CDCl$_3$) δ 8.30 (d, J=4.0 Hz, 1H), 7.44-7.58 (m, 5H), 7.24-7.31 (m, 2H), 7.21 (d, J=7.8 Hz, 1H), 7.00-7.06 (m, 1H), 6.97 (d, J=8.3 Hz, 2H), 5.10 (d, J=9.1 Hz, 1H), 4.61 (td, J=12.1, 6.1 Hz, 1H), 4.43 (t, J=12.8 Hz, 1H), 3.74-3.86 (m, 1H), 3.20 (dd, J=13.8, 3.7 Hz, 1H), 2.67-2.79 (m, 1H), 1.99-2.07 (m, 2H), 1.58-1.68 (m, 2H), 1.49 (s, 9H), 1.39 (d, J=6.1 Hz, 6H), 1.04-1.19 (m, 1H), 0.91 (d, J=6.8 Hz, 3H), 0.87 (t, J=7.3 Hz, 3H); LRMS (ESI) m/e 572.3 [(M+H)$^+$, calcd for C$_{35}$H$_{46}$N$_3$O$_4$ 572.3].

Part B. (1R,2R)-2-Pyridin-2-yl-cyclopropanecarboxylic acid ((2S,3S)-2-amino-3-methyl-pentyl)-(4'-isopropoxy-biphenyl-4-yl)-amide A solution of ((1S,2S)-1-{[(4'-isopropoxy-biphenyl-4-yl)-(2-pyridin-2-yl-cyclopropanecarbonyl)-amino]-methyl}-2-methyl-butyl)-carbamic acid tert-butyl ester (48 mg, 0.084 mmol) and dichloromethane (4 mL) was treated with a solution of HCl in dioxane (4 N, 0.5 mL) and the resulting reaction mixture was maintained at room temperature for 12 h. The reaction was then concentrated to dryness to afford (1R,2R)-2-pyridin-2-yl-cyclopropanecarboxylic acid ((2S,3S)-2-amino-3-methyl-pentyl)-(4'-isopropoxy-biphenyl-4-yl)-amide (38 mg, 95% yield) as a white solid: $^1$H NMR (400 MHz, MeOD) δ 8.34 (d, J=5.3 Hz, 1H), 7.95 (t, J=7.6 Hz, 1H), 7.55 (d, J=8.1 Hz, 2H), 7.38-7.45 (m, 3H), 7.29-7.37 (m, 3H), 6.88 (d, J=8.6 Hz, 2H), 4.54 (dt, J=12.1, 6.1 Hz, 1H), 4.22 (dd, J=15.0, 9.0 Hz, 1H), 3.65 (dd, J=15.0, 2.7 Hz, 1H), 3.23-3.30 (m, 1H), 2.66-2.76 (m, 1H), 1.99-2.06 (m, 1H), 1.72-1.80 (m, 1H), 1.63-1.71 (m, 1H), 1.45-1.54 (m, 1H), 1.26-1.36 (m, 1H), 1.24 (d, J=6.1 Hz, 6H), 1.05-1.17 (m, 1H), 0.88 (d, J=6.8 Hz, 3H), 0.75 (t, 3H); LRMS (ESI) m/e 472.3 [(M+H)$^+$, calcd for $C_{30}H_{38}N_3O_2$ 472.3].

Example 3

(1R,2R)-2-Pyridin-2-yl-cyclopropanecarboxylic acid ((2S,3S)-2-amino-3-methyl-pentyl)-(4'-propylbiphenyl-4-yl)-amide

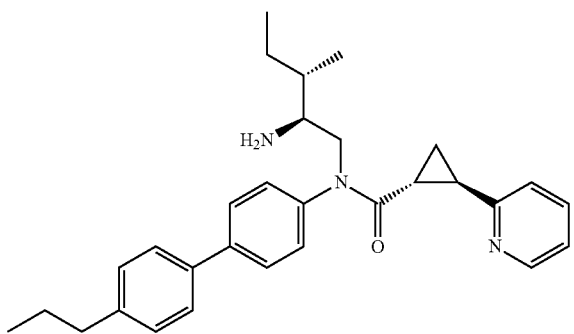

Part A. ((1S,2S)-1-{[(4'-Propyl-biphenyl-4-yl)-((1R,2R)-2-pyridin-2-yl-cyclopropanecarbonyl)-amino]-methyl}-2-methyl-butyl)-carbamic acid tert-butyl ester A mixture of [(R)-3-(4-bromo-phenyl)-1-((S)-sec-butyl)-4-oxo-4-((1R,2R)-2-pyridin-2-yl-cyclopropyl)-butyl]-carbamic acid tert-butyl ester (68 mg, 0.13 mmol), 4-propyl phenylboronic acid (36 mg, 0.20 mmol), dichloro[1,1'-bis(diphenylphosphino)ferrocene]palladium (II) dichloromethane adduct (10 mg, 0.013 mmol), potassium phosphate (83 mg, 0.39 mmol), dimethoxyethane (1.5 mL) and water (0.5 mL) was heated in a sealed vessel by microwave irradiation at 160° C. for 5 min. The resulting mixture was poured into 1 N aqueous sodium hydroxide solution (15 mL) and extracted with dichloromethane (3×15 mL). Combined organics were dried (MgSO$_4$), filtered and concentrated under reduced pressure to afford a residue that was purified by preparative HPLC (neutral mobile phase) to afford ((1S,2S)-1-{[(4'-propyl-biphenyl-4-yl)-((1R,2R)-2-pyridin-2-yl-cyclopropanecarbonyl)-amino]-methyl}-2-methyl-butyl)-carbamic acid tert-butyl ester (48 mg, 65% yield) as a colorless oil: $^1$H NMR (400 MHz, CDCl$_3$) δ 8.29 (d, J=4.0 Hz, 1H), 7.46-7.59 (m, 5H), 7.24-7.34 (m, 4H), 7.21 (d, J=7.6 Hz, 1H), 6.96-7.04 (m, 1H), 5.10 (d, J=9.1 Hz, 1H), 4.43 (t, J=12.8 Hz, 1H), 3.76-3.87 (m, 1H), 3.20 (dd, J=13.9, 3.5 Hz, 1H), 2.68-2.75 (m, 1H), 2.65 (t, J=7.6 Hz, 2H), 1.98-2.05 (m, 1H), 1.65-1.76 (m, 2H), 1.59-1.65 (m, 1H), 1.49 (s, 11H), 1.07-1.18 (m, 1H), 1.00 (t, J=7.3 Hz, 3H), 0.91 (d, J=6.6 Hz, 3H), 0.88 (t, J=7.3 Hz, 3H); LRMS (ESI) m/e 556.3 [(M+H)$^+$, calcd for $C_{35}H_{46}N_3O_3$ 556.4].

Part B. (1R,2R)-2-Pyridin-2-yl-cyclopropanecarboxylic acid ((2S,3S)-2-amino-3-methyl-pentyl)-(4'-propyl-biphenyl-4-yl)-amide A solution of ((1S,2S)-1-{[(4'-propyl-biphenyl-4-yl)-(2-pyridin-2-yl-cyclopropanecarbonyl)-amino]-methyl}-2-methyl-butyl)-carbamic acid tert-butyl ester (48 mg, 0.084 mmol) and dichloromethane (4 mL) was treated with a solution of HCl in dioxane (4 N, 0.5 mL) and the resulting reaction mixture was maintained at room temperature for 12 h. The reaction was then concentrated to dryness to afford (1R,2R)-2-pyridin-2-yl-cyclopropanecarboxylic acid ((2S,3S)-2-amino-3-methyl-pentyl)-(4'-propyl-biphenyl-4-yl)-amide (38 mg, 95% yield) as a white solid: $^1$H NMR (400 MHz, MeOD) δ 8.31 (d, J=5.1 Hz, 1H), 7.86-7.95 (m, 1H), 7.57 (d, J=8.1 Hz, 2H), 7.33-7.43 (m, 5H), 7.30 (d, J=8.1 Hz, 1H), 7.17 (d, J=8.1 Hz, 2H), 4.21 (dd, J=14.9, 9.1 Hz, 1H), 3.65 (d, J=14.9 Hz, 1H), 3.23-3.29 (m, 1H), 2.64-2.73 (m, 1H), 2.53 (t, J=7.6 Hz, 2H), 1.96-2.05 (m, 1H), 1.70-1.78 (m, 1H), 1.61-1.70 (m, 1H), 1.57 (dd, J=15.2, 7.6 Hz, 2H), 1.43-1.51 (m, 1H), 1.22-1.36 (m, 1H), 1.05-1.17 (m, 1H), 0.82-0.90 (m, 6H), 0.75 (t, J=7.3 Hz, 3H); LRMS (ESI) m/e 456.3 [(M+H)$^+$, calcd for $C_{30}H_{38}N_3O$ 456.3].

Example 4

(Trans)-2-(5-fluoro-pyridin-2-yl)-cyclopropanecarboxylic acid ((2S,3S)-2-amino-3-methyl-pentyl)-(4'-methoxymethyl-biphenyl-4-yl)-amide

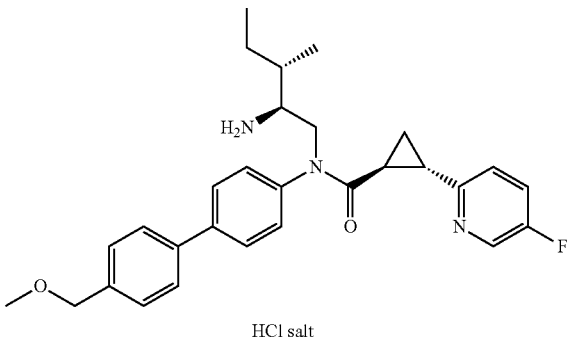 [SMILES: CC[C@H](C)[C@H](N)CN(C(=O)[C@H]1C[C@@H]1c1ccc(F)cn1)c1ccc(-c2ccc(COC)cc2)cc1]

HCl salt

Part A. [(1S,2S)-1-({(4-Bromo-phenyl)-[(trans)-2-(5-fluoro-pyridin-2-yl)-cyclopropane-carbonyl]-amino}-methyl)-2-methyl-butyl]-carbamic acid tert-butyl ester A suspension of the 2-(5-fluoro-pyridin-2-yl)-cyclopropanecarboxylic acid (301 mg, 1.38 mmol) in excess thionyl chloride (10 mL) was refluxed for 1 hr. The solvent was then removed on the rotavap, and further put on the high vacuum pump for 1 hr. The resulting acid chloride was dissolved in 20 mL of DCM, and then the amine (510 mg, 1.38 mmol) was added, followed by TEA (0.4 mL, 2.8 mmol) at rt. The resulting mixture was stirred for 2 hr at rt. It was then diluted with 50 mL of DCM, filter through a thin pad of silica gel, and concentrated. It was purified on the ISCO eluting with 2-30% EtOAc/Hex to give 596 mg (81%) of the desired product.

Part B. ((1S,2S)-1-{[[(trans)-2-(5-Fluoro-pyridin-2-yl)-cyclopropanecarbonyl]-(4'-methoxymethyl-biphenyl-4-yl)-amino]-methyl}-2-methyl-butyl)-carbamic acid tert-butyl ester To 80 mg (0.15 mmol) of the aryl bromide, [(1S,2S)-1-({(4-bromo-phenyl)-[(trans)-2-(5-fluoro-pyridin-2-yl)-cyclopropanecarbonyl]-amino}-methyl)-2-methyl-butyl]-carbamic acid tert-butyl ester, in a microwave vial was added boronic acid (26 mg, 0.158 mmol), $K_2CO_3$ (41.5 mg, 0.301 mmol), $PdCl_2(PPh_3)_2$ (5.3 mg, 0.008 mmol), 6 mL of MeCN, and 1 mL of water. The resulting mixture was microwaved at 140° C. for 30 min. It was then diluted with EtOAc, washed with water, brine and concentrated, and then purified in the neutral PREP HPLC to give 62 mg (72%) of the desired product.

Part C. (1S,2R)-2-(5-Fluoro-pyridin-2-yl)-cyclopropanecarboxylic acid ((2S,3S)-2-amino-3-methyl-pentyl)-(4'-methoxymethyl-biphenyl-4-yl)-amide To 40 mg (0.07 mmol) of ((1S,2S)-1-{[[(trans)-2-(5-fluoro-pyridin-2-yl)-cyclopropanecarbonyl]-(4'-methoxymethyl-biphenyl-4-yl)-amino]-methyl}-2-methyl-butyl)-carbamic acid tert-butyl ester, dissolved in 2 mL of DCM, was added excess (2 mL) of TFA. After 1 hr stirring, it was concentrated on the rotavap, and also on the high vacuum pump, to give 49 mg (100%) of the di-TFA salt. $^1$H NMR (400 MHz, MeOD) δ ppm 8.13 (br. s., 1H), 7.71 (d, J=10.8 Hz, 4H), 7.59 (t, J=7.5 Hz, 4H), 7.42 (dd, J=7.7, 3.3 Hz, 2H), 7.05-7.24 (m, 1H), 4.48 (d, J=2.0 Hz, 2H), 3.69-3.77 (m, 1H), 3.63-3.69 (m, 2H), 3.53-3.59 (m, 1H), 3.39 (d, J=1.6 Hz, 3H), 2.96 (br. s., 1H), 2.16 (br. s., 1H), 1.80 (br. s., 2H), 1.65 (br. s., 1H), 1.40 (br. s., 1H), 1.23 (br. s., 1H), 0.98 (dd, J=11.4, 6.9 Hz, 3H), 0.84 (ddd, J=15.0, 7.4, 7.2 Hz, 3H); m/e LCMS 476.2 [(M+1)$^+$, calcd for $C_{29}H_{35}FN_3O_2$ 476.2].

Example 5

(1R,2R)-2-pyridin-2-yl-cyclopropanecarboxylic acid ((2S,3S)-2-amino-3-methyl-pentyl)-(4'-prop-1-ynyl-biphenyl-4-yl)-amide

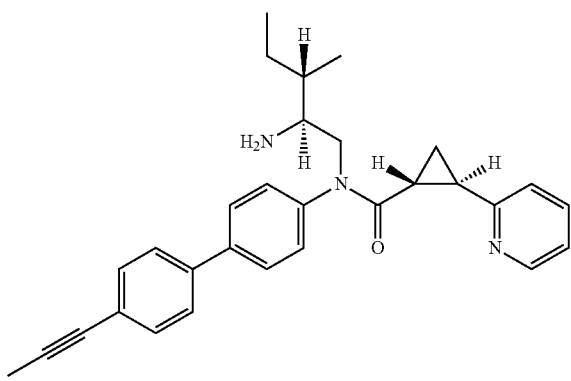 [SMILES: CC#Cc1ccc(-c2ccc(N(C[C@@H](N)[C@@H](C)CC)C(=O)[C@@H]3C[C@H]3c3ccccn3)cc2)cc1]

Part A: 1-bromo-4-prop-1-ynyl-benzene

To a solution of 1-bromo-4-ethynyl-benzene (500 mg, 2.8 mmol) in tetrahydrofuran (20 mL) at −30° C. was slowly added sodium bis(trimethylsilyl)amide in tetrahydrofuran solution (1M, 4.2 mL). After stirring 15 min, methyl iodide (1.1 g, 8.4 mmol) was added at −20° C. The resulting reaction mixture was stirred at RT for 50 min before it was added to water. The mixture was extracted with ethyl acetate and the organic phase was dried over magnesium sulfate and concentrated. The crude product 1-bromo-4-prop-1-ynyl-benzene was obtained as a volatile liquid (450 mg, 82.8% yield) which was put to next step directly without further purification. $^1$H NMR (400 MHz, MeOD) δ ppm 7.34 (d, J=8.3 Hz, 10H), 7.14 (d, J=8.3 Hz, 10H), 1.91 (s, 3H); GCMS, (M+1)=195.1, Molecular Formula=$C_9H_7Br$.

Part B: 4,4,5,5-tetramethyl-2-(4-prop-1-ynyl-phenyl)-[1,3,2]dioxaborolane

A mixture of 1-bromo-4-prop-1-ynyl-benzene (900 mg, 4.63 mmol), [1,1'-bis(diphenylphosphino)ferrocene]dichloropalladium(II), complex with dichloromethane (1:1) (23 mg, 0.23 mmol), bis(pinacolato)diboron (1.78 g, 1.78 mmol) and potassium acetate (1.9 g, 13.89 mmol) in dioxane (20 mL) was stirred at 85° C. and the reaction was completed in 24 hrs. The reaction mixture was diluted with water and extracted with ethyl acetate. Organic layer was dried over magnesium sulfate and concentrated. The residue was purified via column chromatography on silica gel to afford 4,4,5,5-tetramethyl-2-(4-prop-1-ynyl-phenyl)-[1,3,2]dioxaborolane (550 mg, 50% yield). 1H NMR (400 MHz, CDCl$_3$) δ ppm 7.64 (d, J=7.8 Hz, 2H), 7.31 (d, J=8.1 Hz, 2H), 1.99 (s, 3H), 1.27 (s, 12H); GCMS, (M+1)=243.30, Molecular Formula =$C_{15}H_{19}BO_2$

Part C: ((1S,2S)-2-methyl-1-{[(4'-prop-1-ynyl-biphenyl-4-yl)-((1R,2R)-2-pyridin-2-yl-yclopropanecarbonyl)-amino]-methyl}-butyl)-carbamic acid tert-butyl ester A suspension of ((1S,2S)-1-{[(4-bromo-phenyl)-((1R,2R)-2-pyridin-2-yl-cyclopropanecarbonyl)-amino]-methyl}-2-methyl-butyl)-carbamic acid tert-butyl ester (300 mg, 0.58 mmol), 4,4,5,5-tetramethyl-2-(4-prop-1-ynyl-phenyl)-[1,3,2]dioxaborolane (280 mg, 1.16 mmol), [1,1'-bis(diphenylphosphino)ferrocene]dichloropalladium(II), complex with dichloromethane (1:1) (43 mg, 0.058 mmol) and potassium phosphate in 1,2-dimethoxyethane (3 mL) and water (1 mL) was subjected to microwave heating at 160° C. for 5 mins. The reaction mixture was washed by sodium hydroxide (1 N, aq) before it was extracted with ethyl acetate. Organic layer was dried over magnesium sulfate and concentrated. The residue was purified via column chromatography on silica gel to afford ((1S,2S)-2-methyl-1-{[(4'-prop-1-ynyl-biphenyl-4-yl)-((1R,2R)-2-pyridin-2-yl-yclopropanecarbonyl)-amino]-methyl}-butyl)-carbamic acid tert-butyl ester (160 mg, 50% yield). $^1$H NMR (400 MHz, CDCl$_3$) δ ppm 8.19 (d, J=4.5 Hz, 1H), 7.33-7.51 (m, 7H), 7.22 (d, J=7.6 Hz, 2H), 7.12 (d, J=7.8 Hz, 1H), 6.92 (dd, J=6.9, 5.2 Hz, 1H), 4.98 (d, J=9.1 Hz, 1H), 4.33 (t, J=12.9 Hz, 1H), 3.64-3.78 (m, 1H), 3.11 (dd, J=13.8, 3.6631 Hz, 1H), 2.54-2.69 (m, 1H), 2.01 (s, 3H), 1.87-1.96 (m, 1H), 1.52 (dt, J=8.6, 4.3 Hz, 1H), 1.29-1.48 (m, 12H), 0.93-1.11 (m, 1H), 0.73-0.87 (m, 6H); LRMS (ESI) (M+1)=552.25, Molecular Formular=$C_{35}H_{41}N_3O_3$. $^{13}$C NMR (100 MHz, CHLOROFORM-d) δ ppm 173.73, 159.73, 156.71, 141.71, 140.32, 139.46, 132.37, 128.58, 127.21, 123.78, 123.06, 121.38, 87.22, 79.88, 79.16, 54.44, 50.46, 38.56, 28.88, 27.64, 25.63, 25.12, 18.50, 15.45, 12.15, 4.80.

Part D: (1R,2R)-2-pyridin-2-yl-cyclopropanecarboxylic acid ((2S,3S)-2-amino-3-methyl-pentyl)-(4'-prop-1-ynyl-biphenyl-4-yl)-amide At 0° C., acetyl chloride (227.6 mg, 2.9 mmol) was added to ((1S,2S)-2-methyl-1-{[(4'-prop-1-ynyl-biphenyl-4-yl)-((1R,2R)-2-pyridin-2-yl-yclopropanecarbonyl)-amino]-methyl}-butyl)-carbamic acid tert-butyl ester (169 mg, 0.29 mmol) in methanol (3 mL) slowly. The resulting reaction mixture was stirred at RT for 4 h and the reaction was completed. The reaction mixture was concentrated down and the residue was purified by prep-HPLC to obtain (1R,2R)-2-pyridin-2-yl-cyclopropanecarboxylic acid ((2S,3S)-2-amino-3-methyl-pentyl)-(4'-prop-1-ynyl-biphenyl-4-yl)-amide as light brown solid (110 mg, 67% yield, trifluoroacetic acid salt). $^1$H NMR (400 MHz, MeOD) δ ppm 8.46-8.65 (m, 1H), 8.11-8.33 (m, 1H), 7.62-7.78 (m, 3H), 7.47-7.60 (m, 5H), 7.45 (d, J=8.3 Hz, 2H), 4.32 (dd, J=15.0, 9.0 Hz, 1H), 3.81 (dd, J=14.9, 2.3 Hz, 1H), 3.36-3.44 (m, 1H), 2.85-2.98 (m, 1H), 2.10-2.20 (m, 1H), 2.06 (s, 3H), 1.90-2.00 (m, 1H), 1.72-1.86 (m, 1H), 1.63-1.72 (m, 1H), 1.35-1.51 (m, 1H), 1.15-1.32 (m, 1H), 0.98 (d, J=6.8 Hz, 3H), 0.87 (t, J=7.3 Hz, 3H); LRMS (ESI)=452.2, [(M+H)$^+$, Calcd for $C_{30}H_{34}N_3O$ 452.6]; $^{13}$C NMR (100 MHz, MeOD) δ ppm 173.85, 158.36, 142.49, 142.45, 140.15, 133.58, 130.11, 129.94, 128.23, 125.6, 125.63, 125.02, 88.14, 80.51, 56.93, 51.15, 37.66, 27.68, 26.80, 25.76, 18.50, 14.49, 12.07, 4.23.

Example 6

Trans-2-(6-fluoro-pyridin-2-yl)-cyclopropanecarboxylic acid (1-amino-cyclopentylmethyl)-(4'-propyl-biphenyl-4-yl)-amide

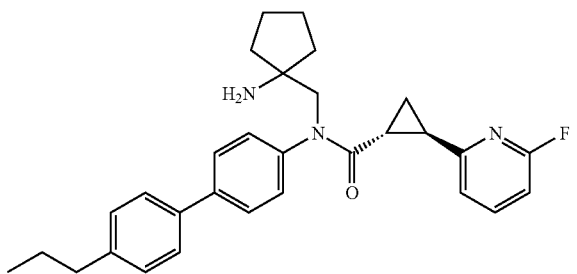 [SMILES: CCCc1ccc(-c2ccc(N(CC3(N)CCCC3)C(=O)[C@@H]3C[C@H]3c3cccc(F)n3)cc2)cc1]

Part A: 2-Fluoro-6-oxiranyl-pyridine

A mixture of 6-fluoro-pyridine-2-carbaldehyde (1.88 g, 15 mmol), trimethylsulfonium iodide (3.3 g, 16.2 mmol) and KOH (crashed, 3.46 g, 61.9 mmol) in CH$_3$CN (190 mL, containing 0.2 mL of water) was stirred at 65-70° C. under N$_2$ for overnight. The mixture was cooled to rt and diluted with EtOAc (100 mL). After filtration, the filtrate was concentrated. The residue was portioned between H$_2$O (100 mL) and EtOAc (80 mL), the aqueous layer was further extracted with EtOAc (4×80 mL). the combined EtOAc was dried (Na$_2$SO$_4$) and concentrated. The residue was subjected to ISCO (40 g column, hexane 3 min. then 0-60% EtOAc in hexane over 60 min.) to give the desired product (530 mg).

Part B: Trans-2-(6-fluoro-pyridin-2yl)-cyclopropanecarboxylic acid tert-butyl ester To a suspension of NaH (60% oil dispersion, 320 mg, 8 mmol) in toluene (10 mL) was added dropwise t-butyl diethylphosphonoacetate (1.92 g, 7.6 mmol). The resulting mixture was stirred at rt for 10 min., then a solution of 2-fluoro-6-oxiranyl-pyridine (530 mg, 3.8 mmol) in toluene (5 mL) was added dropwise to the reaction mixture. The resulting mixture was then heated at reflux for 12 h. The mixture was cooled to rt and diluted with EtOAc and washed with NH$_4$Cl (saturated) and water. The EtOAc layer was dried (Na$_2$SO$_4$). The solvent was removed and the residue was subjected to ISCO (40 g column, hexane 3 min. then 0-60% EtOAc in hexane over 60 min.) to give the desired product (165 mg). MS (MH$^+$ 238).

Part C: Trans-2-(6-fluoro-pyridin-2yl)-cyclopropanecarboxylic acid

To a solution of trans-2-(6-fluoro-pyridin-2-yl)-cyclopropanecarboxylic acid t-butyl ester (165 mg, 0.7 mmol) in DCM (3 mL) was added HCl in dioxane (4 M, 10 mL). The resulting mixture was stirred at rt for 3 h. The mixture was then concentrated to give the desired product as HCl salt (120 mg, 79%). MS (M−H 181).

Part D: {1-[(4-Bromo-phenylamino)-methyl]-cyclopentyl}-carbamic acid tert-butyl ester To a solution of N-Boc-cycloleucinal (5.33 g, 25 mmol) and 4-bromoaniline (4.3 g, 25 mmol) in dichloroethane (160 mL) was added sodium triacetoxyborohydride (10.6 g, 50 mmol) portionwise. After the addition, the resulting mixture was stirred at rt for over night. The reaction mixture was quenched with saturated NaHCO$_3$, and extracted with DCM (4×100 mL). The combined DCM was dried (Na$_2$SO$_4$) and concentrated. The residue was subjected to flash column (10-30% EtOAc in hexane) to give the desired product as a white solid (8.3 g, 90%). MS (MH$^+$ 369 and 371).

Part E: [1-({(4-Bromo-phenyl)-[trans-2-(6-fluoro-pyridin-2-yl)-cyclopropanecarbonyl]-amino}-methyl)-cyclopentyl]-carbamic acid tert-butyl ester A mixture of trans-2-(6-fluoro-pyridin-2yl)-cyclopropanecarboxylic acid (~0.9 mmol) in thionyl chloride (2 mL) was heated at reflux for overnight. The mixture was concentrated and dried under high vacuum for 2 h. Then the residue was dissolved in DCM (4 mL) and added dropwise to a solution of {1-[(4-Bromo-phenylamino)-methyl]-cyclopentyl}-carbamic acid tert-butyl ester (370 mg, 1 mmol) and triethyl amine (280 uL) in DCM (4 mL). The resulting mixture was stirred at rt for over night. The reaction mixture was subjected to flash column directly (20% EtOAc in hexane) to give the desired product as a white solid (348 mg, ~70%). MS (MH$^+$ 532 and 534).

Part F: (1-{[[Trans-2-(6-fluoro-pyridin-2-yl)-cyclopropanecarbonyl]-(4'-propyl-biphenyl-4-yl)-amino]-methyl}-cyclopentyl)-carbamic acid tert-butyl ester A mixture of [1-({(4-Bromo-phenyl)-[trans-2-(6-fluoro-pyridin-2-yl)-cyclopropanecarbonyl]-amino}-methyl)-cyclopentyl]-carbamic acid t-butyl ester (95 mg, 0.18 mmol), arylboronic acid (0.22 mmol), Pd(PPh$_3$)$_2$Cl$_2$ (14 mg, 0.02 mmol) and K$_2$CO$_3$ (47 mg, 0.34 mmol) in CH$_3$CN/H$_2$O (3.5/0.5 mL) was macrowaved at 140° C. for 20 min. The reaction mixture was passed through a short silica pad (EtOAc) and concentrated. The residue was subjected to ISCO (12 g column, 0-50% EtOAc in hexaneover 25 min) to give the desired products. MS (MH$^+$ 572).

Part G: Trans-2-(6-fluoro-pyridin-2-yl)-cyclopropanecarboxylic acid (1-amino-cyclopentylmethyl)-(4'-propyl-biphenyl-4-yl)-amide A solution of above preparation in DCM (1 mL) was treated with TFA/DCM (2/2 mL) for 1 h. The mixture was concentrated to give the desired products as di-TFA salts. $^1$H NMR (400 MHz, MeOD) δ ppm 7.8 (q, J=8.0 Hz, 1H), 7.6 (br. s., 2H), 7.5 (d, J=8.1 Hz, 2H), 7.4 (d, J=6.6 Hz, 2H), 7.3 (d, J=8.1 Hz, 2H), 7.2 (dd, J=7.3, 2.0 Hz, 1H), 6.7 (dd, J=8.1, 2.3 Hz, 1H), 4.1-4.2 (m, 1H), 4.0-4.1 (m, 1H), 2.6-2.7 (m, 3H), 2.0 (t, J=9.0 Hz, 1H), 1.7-1.9 (m, 6H), 1.5-1.7 (m, J=15.0, 7.5, 7.5, 7.3 Hz, 5H), 1.4 (td, J=5.6, 3.0 Hz, 1H), 1.0 (t, J=7.3 Hz, 3H). LRMS (ESI)=472.2, [(M+H)$^+$, Calcd for $C_{30}H_{35}FN_3O$ 472.6].

Example 7

Trans-2-(6-fluoro-pyridin-2-yl)-cyclopropanecarboxylic acid (1-amino-cyclopentylmethyl)-(4'-isopropoxy-biphenyl-4-yl)-amide

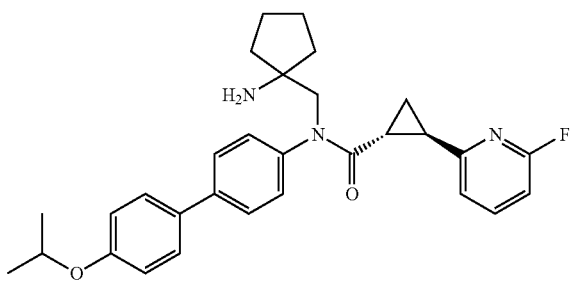 [SMILES: CC(C)Oc1ccc(-c2ccc(N(CC3(N)CCCC3)C(=O)[C@@H]3C[C@H]3c3cccc(F)n3)cc2)cc1]

Part A: (1-{[[Trans-2-(6-fluoro-pyridin-2-yl)-cyclopropanecarbonyl]-(4'-isopropoxy-biphenyl-4-yl)-amino]-methyl}-cyclopentyl)-carbamic acid tert-butyl ester A mixture of [1-({(4-bromo-phenyl)-[trans-2-(6-fluoro-pyridin-2-yl)-cyclopropanecarbonyl]-amino}-methyl)-cyclopentyl]-carbamic acid t-butyl ester (95 mg, 0.18 mmol), arylboronic acid (0.22 mmol), Pd(PPh$_3$)$_2$Cl$_2$ (14 mg, 0.02 mmol) and K$_2$CO$_3$ (47 mg, 0.34 mmol) in CH$_3$CN/H$_2$O (3.5/0.5 mL) was macrowaved at 140° C. for 20 min. The reaction mixture was passed through a short silica pad (EtOAc) and concentrated. The residue was subjected to ISCO (12 g column, 0-50% EtOAc in hexane over 25 min) to give the desired products. MS (MH$^+$ 588).

Part B: Trans-2-(6-fluoro-pyridin-2-yl)-cyclopropanecarboxylic acid (1-amino-cyclopentylmethyl)-(4'-isopropoxy-biphenyl-4-yl)-amide A solution of above preparation in DCM (1 mL) was treated with TFA/DCM (2/2 mL) for 1 h. The mixture was concentrated to give the desired products as di-TFA salts.

$^1$H NMR (400 MHz, MeOD) δ ppm 7.8 (q, J=7.9 Hz, 1H), 7.5 (br. s., 2H), 7.5 (d, J=8.6 Hz, 2H), 7.4 (d, J=5.8 Hz, 2H), 7.2 (dd, J=7.3, 2.3 Hz, 1H), 7.0 (d, J=8.6 Hz, 2H), 6.7 (dd, J=8.2, 2.4 Hz, 1H), 4.6 (dt, J=12.1, 6.1 Hz, 1H), 4.1-4.2 (m, 1H), 4.0-4.1 (m, 1H), 2.6 (t, J=9.3 Hz, 1H), 2.0 (t, J=9.0 Hz, 1H), 1.7-1.9 (m, 6H), 1.7 (ddd, J=9.0, 5.4, 3.8 Hz, 1H), 1.6 (td, J=9.2, 4.8 Hz, 2H), 1.4 (td, J=5.6, 3.0 Hz, 1H), 1.3 (d, J=6.1 Hz, 6H). LRMS (ESI)=488.2, [(M+H)$^+$, Calcd for $C_{30}H_{35}FN_3O_2$ 488.6].

Example 8

Trans-2-(6-fluoro-pyridin-2-yl)-cyclopropanecarboxylic acid (1-amino-cyclopentylmethyl)-(4'-methoxymethyl-biphenyl-4-yl)-amide

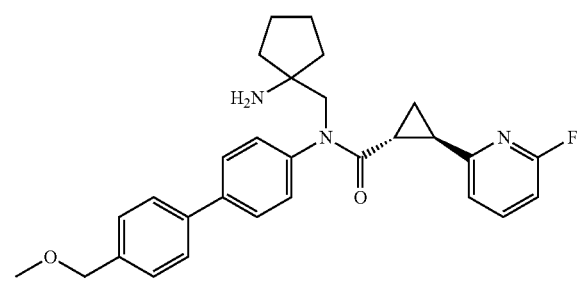 [SMILES: COCc1ccc(-c2ccc(N(CC3(N)CCCC3)C(=O)[C@@H]3C[C@H]3c3cccc(F)n3)cc2)cc1]

Part A. (1-{[[Trans-2-(6-fluoro-pyridin-2-yl)-cyclopropanecarbonyl]-(4'-methoxymethyl-biphenyl-4-yl)-amino]-methyl}-cyclopentyl)-carbamic acid tert-butyl ester A mixture of [1-({(4-bromo-phenyl)-[trans-2-(6-fluoro-pyridin-2-yl)-cyclopropanecarbonyl]-amino}-methyl)-cyclopentyl]-carbamic acid t-butyl ester (95 mg, 0.18 mmol), arylboronic acid (0.22 mmol), Pd(PPh$_3$)$_2$Cl$_2$ (14 mg, 0.02 mmol) and K$_2$CO$_3$ (47 mg, 0.34 mmol) in CH$_3$CN/H$_2$O (3.5/0.5 mL) was macrowaved at 140° C. for 20 min. The reaction mixture was passed through a short silica pad (EtOAc) and concentrated. The residue was subjected to ISCO (12 g column, 0-50% EtOAc in hexane over 25 min) to give the desired products. MS (MH$^+$ 574).

Part B. Trans-2-(6-fluoro-pyridin-2-yl)-cyclopropanecarboxylic acid (1-amino-cyclopentylmethyl)-(4'-methoxymethyl-biphenyl-4-yl)-amide A solution of above preparation in DCM (1 mL) was treated with TFA/DCM (2/2 mL) for 1 h. The mixture was concentrated to give the desired products as di-TFA salts.

$^1$H NMR (400 MHz, MeOD) δ ppm 7.8 (q, J=8.0 Hz, 1H), 7.6 (br. s., 2H), 7.6 (d, J=8.1 Hz, 2H), 7.5 (br. s., 2H), 7.4 (d, J=8.1 Hz, 2H), 7.2 (dd, J=7.5, 2.1 Hz, 1H), 6.7 (dd, J=8.1, 2.3 Hz, 1H), 4.5 (s, 2H), 4.1-4.2 (m, 1H), 4.0-4.1 (m, 1H), 3.4 (s, 3H), 2.6 (t, J=9.3 Hz, 1H), 2.0 (t, J=9.0 Hz, 1H), 1.7-1.9 (m, 6H), 1.7 (ddd, J=8.9, 5.4, 3.9 Hz, 1H), 1.5-1.7 (m, 2H), 1.4 (dd, 1H). LRMS (ESI)=474.2, [(M+H)$^+$, Calcd for $C_{29}H_{32}FN_3O_2$ 473.6].

Example 9

Trans-2-Pyridin-2-yl-cyclopropanecarboxylic acid (4-amino-tetrahydro-pyran-4-ylmethyl)-(4'-propyl-biphenyl-4-yl)-amide

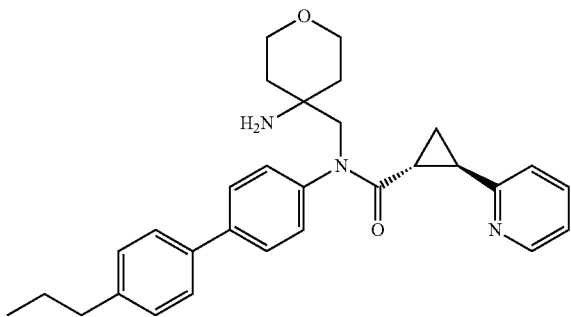 [SMILES: CCCc1ccc(-c2ccc(N(CC3(N)CCOCC3)C(=O)[C@@H]3C[C@H]3c3ccccn3)cc2)cc1]

Part A: (4-Hydroxymethyl-tetrahydro-pyran-4-yl)-carbamic acid tert-butyl ester Neat 4-methylmorpholine (2.7 mL, 24.6 mmol) was added, via syringe, to a rapidly stirred, 0° C., solution of 4-tert-butoxycarbonylamino-tetrahydro-pyran-4-carboxylic acid (5.0 g, 20.4 mmol) and isobutyl chloroformate (3.2 mL, 24.5 mmol) in anhydrous tetrahydrofuran (200 mL) contained in a 1000 mL round bottomed flask. Precipitate immediately formed. The suspension was allowed to stir at 0° C. under $N_2$ blanket for 20 minutes then a hand swirled, gas evolving, suspension of sodium borohydride (2.3 g, 61.3 mmol) in methanol (65 mL) was added, at as fast of a rate as possible while maintaining control of the concomitant reaction foaming. When observable gas evolution had ceased the opaque white reaction suspension was transferred to a separatory funnel containing saturated aqueous sodium chloride (500 mL) and extracted with ethyl acetate. Combined organic extracts were dried ($MgSO_4$), passed through a plug of silica gel, and evaporated to obtain 4.89 g of off white solid which was used without further purification. LRMS (ESI) m/z 232.2 $[(M+H)^+$, calcd for $C_{11}H_{22}NO_4$ 232.3].

Part B: (4-Formyl-tetrahydro-pyran-4-yl)-carbamic acid tert-butyl ester

Anhydrous dimethyl sulfoxide (3.0 mL, 42.2 mmol) was added to a ⁻65° C. solution of oxalyl chloride (2.0 mL, 22.9 mmol) in anhydrous dichloromethane (100 mL) and allowed to stir at ⁻65° C. under $N_2$ blanket for 3 minutes, after which time a solution of (4-hydroxymethyl-tetrahydro-pyran-4-yl)-carbamic acid tert-butyl ester (4.89 g, 21.1 mmol) in anhydrous dichloromethane (25 mL) was added. When 25 minutes had elapsed, triethylamine (14.7 mL, 105.5 mmol) was added and the reaction solution allowed to stir for a further 20 minutes at ⁻65° C.; then the cold bath was removed and the reaction warmed to ambient temperature, washed with saturated aqueous sodium chloride (500 mL), dried ($MgSO_4$), and evaporated to afford 4.48 g of clear yellow viscous liquid which was used without further purification. LRMS (ESI) m/z 230.2 $[(M+H)^+$, calcd for $C_{11}H_{20}NO_4$ 230.3].

Part C: {4-[(4-Bromo-phenylamino)-methyl]-tetrahydro-pyran-4-yl}-carbamic acid tert-butyl ester A solution of (4-formyl-tetrahydro-pyran-4-yl)-carbamic acid tert-butyl ester (4.48 g, 19.5 mmol), 4-bromoaniline (3.38 g, 19.7 mmol), and acetic acid (1.2 mL, 21.2 mmol) in ethyl acetate (50 mL) contained in a 250 mL round bottom flask fitted with a reflux condenser and a Dean and Stark trap was heated at reflux under $N_2$ blanket for 2 h then cooled to ambient temperature. Sodium cyanoborohydride (1.29 g, 19.5 mmol) was added and the mixture stirred over night. The reaction mixture was then washed with water (50 mL), saturated aqueous sodium chloride (50 mL), dried ($MgSO_4$), pre-absorbed on silica gel and flash chromatographed (elution solvent: 10% (v/v) ethyl acetate/hexane) to isolate the desired product as 3.1 g of white solid foam. LRMS (ESI) m/z 385.0, 387.0 $[(M+H)^+$, calcd for $C_{17}H_{26}N_2O_3Br$ 386.3].

Part D: 2-Pyridin-2-yl-cyclopropanecarboxylic acid tert-butyl ester

To a stirred suspension of sodium tert-butoxide (7.63 g, 79.4 mmol) in 1,2-dimethoxyethane (70 mL) at ambient temperature was added tert-butyl diethylphosphonoacetate (20.0 g, 79.4 mmol) over 30 minutes, then allowed to stir a further 40 minutes then 3-(oxiran-2-yl)pyridine (4.8 g, 39.7 mmol) was added drop wise. The suspension was stirred at for 30 minutes then heated to 65° C. overnight. The reaction was poured onto ice and extracted with diethyl ether. The combined organic extracts were washed with saturated aqueous sodium chloride, dried ($MgSO_4$), and evaporated to provide an orange oil which was purified by flash chromatography (elution solvent: 20% (v/v) hexane/dichloromethane) to obtain 3.0 g of purified material.

Part E: 2-Pyridin-2-yl-cyclopropane carboxylic acid

To a solution of 2-pyridin-2-yl-cyclopropanecarboxylic acid tert-butyl ester (1.6 g, 7.3 mmol) in dichloromethane (30 mL) was added a solution of anhydrous HCl in dioxane (4.0M, 15 mL). The solution was allowed to stir at ambient temperature overnight then evaporated to yield the product as a yellow oil.

Part F: (4-{[(4-Bromo-phenyl)-(2-pyridin-2-yl-cyclopropanecarbonyl)-amino]-methyl}-tetrahydro-pyran-4-yl)-carbamic acid tert-butyl ester Oxalyl chloride (0.42 mL, 4.8 mmol) was added to a stirred suspension of 2-pyridin-2-yl-cyclopropane carboxylic acid (0.65 g, 3.98 mmol) in anhydrous dichloromethane (40 mL) and anhydrous dimethylformamide (1.0 mL). Neat triethyamine (1.2 mL, 8.6 mmol) was then slowly added and the mixture allowed to stir at ambient temperature for 0.5 h over which time the reaction became blue in color and the solid dispersed. The reaction mixture evaporated to dryness then redissolved in dichloromethane (40 mL). A solution of 2-pyridin-2-yl-cyclopropanecarboxylic acid tert-butyl ester (1.54 g, 3.98 mmol) in dichloromethane (5.0 mL) was slowly added to the dichloromethane solution of the previously formed acid chloride and stirred for 15 minutes then washed with saturated aqueous sodium chloride (50 mL), dried ($MgSO_4$), pre-absorbed on silica gel and flash chromatographed (elution solvent: 60% (v/v) ethyl acetate/hexane) to isolate the desired product as 1.06 g of white solid foam. LRMS (ESI) m/z 530.0, 532.0 $[(M+H)^+$, calcd for $C_{26}H_{33}N_3O_4Br$ 531.5].

Part G: Trans-2-pyridin-2-yl-cyclopropanecarboxylic acid (4-amino-tetrahydro-pyran-4-ylmethyl)-(4'-propyl-biphenyl-4-yl)-amide To a 5 mL glass microwave vial containing a magnetic stir bar was added (4-{[(4-bromo-phenyl)-(2-pyridin-2-yl-cyclopropanecarbonyl)-amino]-methyl}-tetrahydro-pyran-4-yl)-carbamic acid tert-butyl ester (216.3 mg, 0.41 mmol), 4-propyl-phenyl-boronic acid (80.7 mg, 0.49 mmol), tripotassium phosphate (175.0 mg, 0.82 mmol), and [1,1'bis(diphenylphosphino)ferrocene]dichloropalladium(II) complex with dichloromethane (8.2 mg, 0.01 mmol). The vial was closed with a septum and evacuated by cannula whilst the contained mixture stirred. The vessel was N2 blanketed then 1,2-dimethoxyethane (4.1 mL) and water (1.4 mL) were added via syringe.

The stirred reaction solution was then taken through 5 evacuation/$N_2$ blanketing cycles, by cannula, left under $N_2$ blanket, then heated to 85° C. at 5° C. per minute, by proportional wattage microwave irradiation at 2.45 GHz, for a total of 15 minutes. The reaction mixture was then diluted with methanol (50 mL), filtered through celite, preabsorbed on silica gel and flash chromatographed (elution solvent: 15% (v/v) 2-propanol/hexane). Combined chromatography fractions were partially evaporated to result in a 2-propanol solution (30 mL) of the penultimate product. To this solution was added aqueous HCl (0.5 mL, 6M) and the solution allowed to stir at ambient temperature. Thin layer chromatography (elution solvent: 10% (v/v) 2-propanol/hexane) showed the deprotection to be complete within 15 minutes, and the reaction solution was evaporated to dryness then taken up in methanol. This stirred methanol solution was diluted with diethyl ether to precipitate the hydrochloride salt of the desired product as an amorphous white powder, which was isolated by filtration. Filtrand was washed with diethyl ether and dried to afford 135.1 mg of product; m.p. 180-183° C. $^1$H NMR (400 MHz, DMSO-$D_6$): δ ppm 8.54 (d, j=4.3 Hz, 1H), 8.27 (br s, 2H), 8.04-8.17 (m, 1H), 7.68 (d, j=8.3 Hz, 2H), 7.61 (d, j=7.8 Hz, 2H 7.54 (d, j=8.1 Hz, 3H), 7.27 (d, j=8.1 Hz, 2H 4.22 (d, j=15.2 Hz, 1H), 4.09 (d, j=14.9 Hz, 1H), 3.64-3.74 (m, 1H), 3.54-3.64 (m, 1H), 3.32-3.44 (m, 1H), 3.17-3.28 (m, 1H), 2.92-3.05 (m, 1H), 2.59 (t, j=7.3 Hz, 2H), 1.95-2.05 (m, 1H), 1.54-1.84 (m, 8H), 0.91 (t, j=7.3 Hz, 3H). $^{13}$C NMR (100 MHz, $D_6$-DMSO) δ ppm 142.0, 141.9, 141.8, 138.7, 136.1, 128.9, 127.0, 126.4, 123.4, 113.5, 61.7, 61.6, 56.1, 53.4, 36.8, 32.1, 31.7, 25.6, 23.9, 16.6. HRMS (EI-TOF) m/z [M$^+$] calcd for $C_{30}H_{36}N_3O_2$ 470.2808, found 470.2820.

Example 10

(Trans)-2-(3-fluoro-pyridin-2-yl)-cyclopropanecarboxylic acid (2S,3S)-2-amino-3-methyl-pentyl)-(4'-propyl-biphenyl-4-yl)-amide

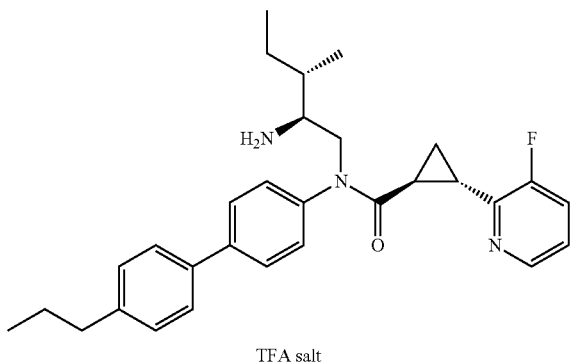 [SMILES: CCCc1ccc(-c2ccc(N(C[C@@H](N)[C@@H](C)CC)C(=O)[C@H]3C[C@@H]3c3ncccc3F)cc2)cc1]

TFA salt

Part A. [(1S,2S)-1-({(4-Bromo-phenyl)-[(trans)-2-(3-fluoro-pyridin-2-yl)-cyclopropane-carbonyl]-amino}-methyl)-2-methyl-butyl]-carbamic acid tert-butyl ester A suspension of 2-(3-fluoro-pyridin-2-yl)-cyclopropanecarboxylic acid (361 mg, 1.66 mmol) in excess thionyl chloride (10 mL) was refluxed for 1 hr. The solvent was then removed on the rotavap, and further put on the high vacuum pump for 1 hr. The resulting acid chloride was dissolved in 20 mL of DCM, and then the amine (612 mg, 1.66 mmol) was added, followed by TEA (0.48 mL, 3.66 mmol) at rt. The resulting mixture was stirred for 2 hr at rt. It was then diluted with 50 mL of DCM, filter through a thin pad of silica gel, and concentrated. It was purified on the ISCO eluting with 2-30% EtOAc/Hex to give 655 mg (89%) of the desired product.

Part B. ((1S,2S)-1-{[[trans)-2-(3-Fluoro-pyridin-2-yl)-cyclopropanecarbonyl]-(4'-propyl-biphenyl-4-yl)-amino]-methyl}-2-methyl-butyl)-carbamic acid tert-butyl ester To 88 mg (0.17 mmol) of the aryl bromide, [(1S,2S)-1-({(4-bromo-phenyl)-[(trans)-2-(3-fluoro-pyridin-2-yl)-cyclopropanecarbonyl]-amino}-methyl)-2-methyl-butyl]-carbamic acid tert-butyl ester, in a microwave vial was added boronic acid (29 mg, 0.174 mmol), $K_2CO_3$ (45.7 mg, 0.331 mmol), PdCl$_2$(PPh$_3$)$_2$ (5.8 mg, 0.009 mmol), 6 mL of MeCN, and 1 mL of water. The resulting mixture was microwaved at 140° C. for 30 min. It was then diluted with EtOAc, washed with water, brine and concentrated, and then purified in the neutral PREP HPLC to give 66 mg (77%) of the desired product.

Part C. (trans)-2-(3-Fluoro-pyridin-2-yl)-cyclopropanecarboxylic acid (2S,3S)-2-amino-3-methyl-pentyl)-(4'-propyl-biphenyl-4-yl)-amide To 56 mg (0.10 mmol) of ((1S,2S)-1-{[[(trans)-2-(3-fluoro-pyridin-2-yl)-cyclopropanecarbonyl]-(4'-propyl-biphenyl-4-yl)-amino]-methyl}-2-methyl-butyl)-carbamic acid tert-butyl ester, dissolved in 3 mL of DCM, was added excess (3 mL) of TFA. After 1 hr stirring, it was concentrated on the rotavap, and also on the high vacuum pump, to give 70 mg (100%) of the di-TFA salt. $^1$H NMR (400 MHz, MeOD) δ ppm 8.05 (dt, J=3.0, 1.5 Hz, 1H), 7.64 (d, J=8.2 Hz, 2H), 7.35-7.54 (m, 5H), 7.26 (dd, J=8.2, 2.4 Hz, 2H), 7.09-7.19 (m, 1H), 4.31 (dd, J=15.0, 9.1 Hz, 1H), 3.65-3.80 (m, 1H), 2.89 (br. s., 1H), 2.62 (t, J=7.5 Hz, 2H), 2.02-2.14 (m, 1H), 1.59-1.81 (m, 4H), 1.30-1.57 (m, 3H), 1.23 (s, 1H), 0.91-1.01 (m, 6H), 0.77-0.88 (m, 3H); m/e LCMS 474.3 [(M+1)$^+$, calcd for $C_{30}H_{37}FN_3O$ 474.4].

Example 11

(Trans)-2-pyrazin-2-yl-cyclopropanecarboxylic acid ((2S,3S)-2-amino-3-methyl-pentyl)-(4'-propyl-biphenyl-4-yl)-amide

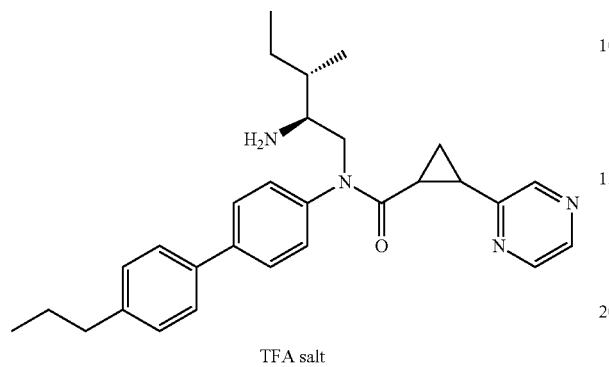

TFA salt

Part A. ((1-trans)-1-{[(4-Bromo-phenyl)-((1R,2R)-2-pyrazin-2-yl-cyclopropanecarbonyl)-amino]-methyl}-2-methyl-butyl)-carbamic acid tert-butyl ester A suspension of (trans)-2-pyrazin-2-yl-cyclopropanecarboxylic acid (277 mg, 1.38 mmol) in excess thionyl chloride (12 mL) was refluxed for 1 hr. It was concentrated on the rotavap, and further put on the high vacuum pump for 1 hr. The resulting acid chloride was dissolved in 25 mL DCM, and then the amine (510 mg, 1.38 mmol) was added, followed by TEA (0.4 mL, 2.8 mmol) at rt. The resulting mixture was stirred for 2.5 hr at rt. It was then diluted with DCM, and filtered through a pad of silica gel, and then concentrated. It was purified on the ISCO eluting with 5-40% EtOAc/Hex to give 614 mg (86%) of the desired product.

Part B. ((1S,2S)-2-Methyl-1-{[(4'-propyl-biphenyl-4-yl)-((1R,2R)-2-pyrazin-2-yl-cyclo-propanecarbonyl)-amino]-methyl}-butyl)-carbamic acid tert-butyl ester To 77.5 mg (0.15 mmol) of ((1trans)-1-{[(4-bromo-phenyl)-((1R,2R)-2-pyrazin-2-yl-cyclopropanecarbonyl)-amino]-methyl}-2-methyl-butyl)-carbamic acid tert-butyl ester, in a microwave vial was added boronic acid (26 mg, 0.158 mmol), $K_2CO_3$ (41.5 mg, 0.301 mmol), $PdCl_2(PPh_3)_2$ (5.3 mg, 0.008 mmol), 6 mL of MeCN, and 1 mL of water. The resulting mixture was microwaved at 140° C. for 30 min. It was then diluted with EtOAc, washed with water, brine and concentrated, and then purified in the neutral PREP HPLC to give 66 mg (79%) of the desired product.

Part C. (trans)-2-Pyrazin-2-yl-cyclopropanecarboxylic acid ((2S,3S)-2-amino-3-methyl-pentyl)-(4'-propyl-biphenyl-4-yl)-amide To 40 mg (0.072 mmol) of ((1S,2S)-2-methyl-1-{[(4'-propyl-biphenyl-4-yl)-((1R,2R)-2-pyrazin-2-yl-cyclo-propanecarbonyl)-amino]-methyl}-butyl)-carbamic acid tert-butyl ester dissolved in 2 mL DCM was added 3 mL (excess) TFA at rt and stirred for 1 hr. It was concentrated to obtain 49 mg (100%) of the di-TFA salt of the desired product. $^1$H NMR (300 MHz, MeOD) δ ppm 8.59 (d, J=8.6 Hz, 1H), 8.30 (br. s., 2H), 7.56-7.72 (m, 2H), 7.37-7.54 (m, 4H), 7.28 (dd, J=8.1, 1.8 Hz, 2H), 4.26-4.43 (m, 1H), 3.74 (dd, J=14.9, 2.5 Hz, 1H), 3.45-3.28 (m, 1H), 2.69-2.83 (m, 1H), 2.64 (t, J=7.5 Hz, 2H), 1.99-2.14 (m, 1H), 1.61-1.83 (m, 4H), 1.32-1.55 (m, 2H), 1.23 (d, J=7.5 Hz, 1H), 0.92-1.03 (m, 6H), 0.86 (q, J=7.1 Hz, 3H); m/e LCMS 457.3 [(M+1)$^+$, calcd for $C_{29}H_{37}N_4O$ 457.3.

Example 12

2-(5-Fluoro-pyridin-2-yl)-cyclopropanecarboxylic acid ((2S,3S)-2-amino-3-methyl-pentyl)-(4-cyclobutylmethoxy-phenyl)-amide

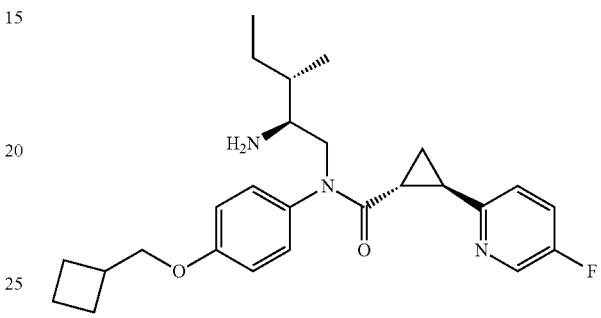

Part A. [(1S,2S)-1-({[4-(tert-Butyl-dimethyl-silanyloxy)-phenyl]-[2-(5-fluoro-pyridin-2-yl)-cyclopropanecarbonyl]-amino}-methyl)-2-methyl-butyl]-carbamic acid tert-butyl ester To 300 mg (1.376 mmol) of the carboxylic acid was added excess thionyl chloride (5 mL) and refluxed for 1 hr. It was concentrated on the rotavap and also put on the high vacuum pump for 1 hr. The acid chloride obtained was dissolved in 20 mL DCM and then 581 mg (1.376 mmol) of the amine was added followed by TEA (0.38 mL, 2.752 mmol). The resulting mixture was stirred at rt for 2 hr, diluted with ether, and quenched with water. The organic layer was washed with water, brine and dried over $MgSO_4$. It was concentrated and purified on the ISCO using 2-30% EtOAc/hex to obtain 627 mg (78%) of the product.

Part B. ((1S,2S)-1-{[[2-(5-Fluoro-pyridin-2-yl)-cyclopropanecarbonyl]-(4-hydroxy-phenyl)-amino]-methyl}-2-methyl-butyl)-carbamic acid tert-butyl ester To the TBS-protected phenol (520 mg, 0.889 mmol) dissolved in 20 mL THF at 0° C., was added 1.78 mL TBAF (1.0 M solution, 1.78 mmol). The ice bath was remove and stirred for 2 hr at rt. It was diluted with ether and quenched with aq. $NH_4Cl$. The organic layer was washed with water and brine, and then dried over $MgSO_4$. It was concentrated and purified on the ISCO using 10-40% EtOAc/hex to obtain 405 mg (97%) of the desired product.

Part C. [(1S,2S)-1-({(4-Cyclobutylmethoxy-phenyl)-[2-(5-fluoro-pyridin-2-yl)-cyclopropanecarbonyl]-amino}-methyl)-2-methyl-butyl]-carbamic acid tert-butyl ester To 70 mg (0.149 mmol) of the phenol compound and cyclobutylmethylbromde (26.5 mg, 0.178 mmol) dissolved in 10 mL DMF was added $K_2CO_3$ (62 mg, 0.446 mmol) and heated to 60° C. overnight. It was cooled to rt, diluted with ether, and quenched with water. The organic layer was washed with water and brine, and then dried over MgSO$_4$. It was concentrated to obtain 80 mg (100%) of the product. No purification was required.

Part D. 2-(5-Fluoro-pyridin-2-yl)-cyclopropanecarboxylic acid ((2S,3S)-2-amino-3-methyl-pentyl)-(4-cyclobutylmethoxy-phenyl)-amide To the Boc-protected amine (80 mg, 0.149 mmol) dissolved in 5 mL DCM was added 5 mL TFA (excess) and stirred for 1 hr at rt. It was concentrated and purified on the acidic PREP HPLC to obtain 48.72 mg (73%) of the di-TFA salt. $^1$H NMR (300 MHz, MeOD) δ ppm 8.20 (dd, J=8.8, 2.9 Hz, 1H), 7.49 (qd, J=8.4, 2.9 Hz, 1H), 7.21-7.35 (m, 3H), 6.94 (d, J=8.6 Hz, 2H), 4.29 (ddd, J=14.8, 13.6, 9.2 Hz, 1H), 3.87-3.97 (m, 2H), 3.62 (ddd, J=15.0, 6.0, 2.7 Hz, 1H), 3.21-3.32 (m, 1H), 2.70-2.84 (m, 1H), 2.63 (dddd, J=14.5, 8.7, 6.0, 4.1 Hz, 1H), 2.07-2.20 (m, 2H), 1.85-2.03 (m, 5H), 1.69-1.79 (m, 1H), 1.57-1.69 (m, 1H), 1.31-1.47 (m, 2H), 1.12-1.29 (m, 1H), 0.97 (dd, J=6.9, 3.8 Hz, 3H), 0.84 (q, J=7.4 Hz, 3H); m/e LCMS 440.2 [(M+1)$^+$, calcd for C$_{26}$H$_{35}$FN$_3$O$_2$ 440.2].

Example 13

(1R,2R)-2-Pyridin-2-yl-cyclopropanecarboxylic acid ((2S,3S)-2-amino-3-methyl-pentyl)-(4-cyclobutylmethoxy-phenyl)-amide

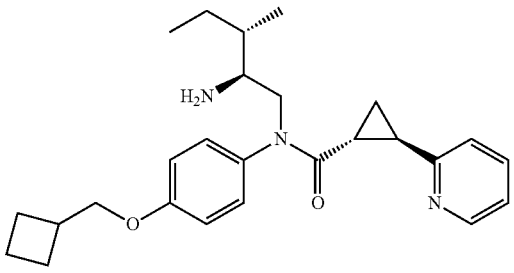 [SMILES: CC[C@H](C)[C@H](N)CN(C(=O)[C@@H]1C[C@H]1c1ccccn1)c1ccc(OCC2CCC2)cc1]

Part A. Tert-butyl (2S,3S)-1-(N-(4-(tert-butyldimethylsilyloxy)phenyl)-trans-2-(pyridin-2-yl)cyclopropanecarboxamido)-3-methylpentan-2-ylcarbamate A solution of trans-2-pyridin-2-yl-cyclopropylcarboxylic acid (270 mg, 1.7 mmol) and dichloromethane (15 mL) was treated with oxalyl chloride (170 µL, 2.0 mmol) and DMF (1 drop). The resulting reaction mixture was maintained at 35° C. for 3 h, then concentrated under reduced pressure to dryness. The residue was dissolved in dichloromethane (15 mL), and treated with tert-butyl (2S,3S)-1-(4-(tert-butyldimethylsilyloxy)phenylamino)-3-methylpentan-2-ylcarbamate (700 mg, 1.7 mmol) and triethylamine (690 µL, 5.0 mmol). The reaction mixture was maintained at room temperature overnight, then diluted with diethyl ether (30 mL) washed with saturated aqueous sodium bicarbonate (30 mL) and brine (30 mL), then dried over MgSO$_4$, filtered and concentrated to afford a residue that was purified by column chromatography on silica gel (eluting with 15% ethyl acetate in hexanes) to afford tert-butyl (2S,3S)-1-(N-(4-(tert-butyldimethylsilyloxy)phenyl)-trans-2-(pyridin-2-yl)cyclopropanecarboxamido)-3-methylpentan-2-ylcarbamate (720 mg, 77% yield) as a yellow oil: $^1$H NMR (400 MHz, CDCl$_3$) δ 8.04-8.13 (m, 1H), 7.25-7.36 (m, 1H), 6.91-7.00 (m, 1H), 6.87-6.91 (m, 1H), 6.76-6.86 (m, 2H), 6.55-6.62 (m, 1H), 6.46-6.55 (m, 1H), 4.83-4.98 (m, 1H), 4.15-4.27 (m, 1H), 3.45-3.64 (m, 1H), 2.81-2.93 (m, 1H), 2.23-2.48 (m, 1H), 1.68-1.81 (m, 1H), 1.37 (s, 3H), 1.29-1.52 (m, 2H), 1.28 (s, 3H), 1.25 (s, 3H), 1.15-1.22 (m, 1H), 0.86-0.97 (m, 1H), 0.78 (d, J=5.1 Hz, 9H), 0.67-0.71 (m, 3H), 0.60-0.67 (m, 3H), −0.06-0.02 (m, 6H); LRMS (ESI) m/e 568.3 [(M+H)$^+$, calcd for C$_{32}$H$_{50}$N$_3$O$_4$Si 568.3].

Part B. Tert-butyl (2S,3S)-1-((1R,2R)—N-(4-hydroxyphenyl)-2-(pyridin-2-yl)cyclopropanecarboxamido)-3-methylpentan-2-ylcarbamate A solution of tert-butyl (2S,3S)-1-(N-(4-(tert-butyldimethylsilyloxy)phenyl)-trans-2-(pyridin-2-yl)cyclopropanecarboxamido)-3-methylpentan-2-ylcarbamate (720 mg, 1.3 mmol) and tetrahydrofuran (25 mL) was treated with tetrabutylammonium fluoride (1 M THF solution, 2.5 mL, 2.5 mmol). The reaction was maintained at room temperature for 2 h, then concentrated under reduced pressure to afford an oil that was purified by column chromatography on silica gel (eluting with 40% ethyl acetate in hexanes) to afford a mixture of diastereomers that was purified by chiral chromatography [Column: ChiralPak AD-H 4.6×250 mm, 25% solvent B (60% Ethanol in hexane) in solvent A (hexane) isocratic, retention time: 6.08 min.] to afford tert-butyl (2S,3S)-1-((1R,2R)—N-(4-hydroxyphenyl)-2-(pyridin-2-yl)cyclopropanecarboxamido)-3-methylpentan-2-ylcarbamate as an oil: $^1$H NMR (300 MHz, CDCl$_3$) δ 8.96 (br. s., 1H), 8.12 (d, J=4.8 Hz, 1H), 7.39 (t, J=7.7 Hz, 1H), 7.09 (d, J=7.8 Hz, 1H), 6.79-6.95 (m, 3H), 6.54 (d, J=8.4 Hz, 2H), 5.13 (d, J=9.2 Hz, 1H), 4.28 (t, J=12.8 Hz, 1H), 3.49-3.66 (m, 1H), 2.87 (dd, J=13.6, 3.7 Hz, 1H), 2.47-2.61 (m, 1H), 1.84-1.98 (m, 1H), 1.38-1.47 (m, 1H), 1.32 (s, 9H), 1.23-1.28 (m, 1H), 0.85-1.01 (m, 1H), 0.73 (d, J=6.9 Hz, 3H), 0.68 (t, J=7.4 Hz, 3H); LRMS (ESI) m/e 454.2 [(M+H)$^+$, calcd for C$_{26}$H$_{36}$N$_3$O$_4$ 454.3].

Part C. (1R,2R)-2-Pyridin-2-yl-cyclopropanecarboxylic acid ((2S,3S)-2-amino-3-methyl-pentyl)-(4-cyclobutylmethoxy-phenyl)-amide A mixture of tert-butyl (2S,3S)-1-((1R,2R)—N-(4-hydroxyphenyl)-2-(pyridin-2-yl)cyclopropanecarboxamido)-3-methylpentan-2-ylcarbamate (69 mg, 0.15 mmol), potassium carbonate (63 mg, 0.46 mmol) and DMF (3 mL) was treated with cyclobutylmethyl bromide (21 µL, 0.18 mmol). The resulting reaction mixture was maintained at 70° C. with vigorous stirring overnight. The mixture was allowed to cool to room temperature, then partitioned between H$_2$O (30 mL) and diethyl ether (20 mL). The layers were separated and the aqueous layer was extracted with diethyl ether (2×20 mL). Combined organics were washed with H$_2$O (30 mL) and brine (30 mL), then dried over Na$_2$SO$_4$, filtered and concentrated under reduced pressure to afford a residue that was purified by column chromatography on silica gel (eluting with 30% ethyl acetate in hexanes) to afford an oil that was dissolved in methanol (2 mL) and cooled to 0° C. The cold solution was then treated dropwise with acetyl chloride (290 µL, 4.0 mmol), and then maintained at room temperature overnight. The reaction was concentrated to dryness to afford (1R,2R)-2-pyridin-2-yl-cyclopropanecarboxylic acid ((2S,3S)-2-amino-3-methyl-pentyl)-(4-cyclobutylmethoxy-phenyl)-amide (56 mg, 88% yield) as a white solid: $^1$H NMR (400 MHz, MeOD) δ 8.61 (d, J=5.3 Hz, 1H), 8.34 (t, J=8.3 Hz, 1H), 7.79 (t, J=6.7 Hz, 1H), 7.54 (d, J=8.3 Hz, 1H), 7.37 (d, J=8.6 Hz, 2H), 6.99 (d, J=8.3 Hz, 2H), 4.28 (dd, J=14.9, 8.8 Hz, 1H), 3.94 (d, J=6.6 Hz, 2H), 3.69 (dd, J=14.9, 2.8 Hz, 1H), 3.34-3.39 (m, 1H), 2.86-2.96 (m, 1H), 2.77 (dt, J=14.6, 7.2 Hz, 1H), 2.08-2.21 (m, 3H), 1.85-2.02 (m, 5H), 1.73-1.84 (m, 1H), 1.67 (dt, J=8.8, 5.5 Hz, 1H), 1.33-1.46 (m, 1H), 1.17-1.30 (m, 1H), 0.98 (d, J=6.8 Hz, 3H), 0.87 (t, J=7.5 Hz, 3H); LRMS (ESI) m/e 422.3 [(M+H)$^+$, calcd for $C_{26}H_{36}N_3O_2$ 422.3].

Example 14

Trans-2-(6-fluoro-pyridin-2-yl)-cyclopropanecarboxylic acid ((2S,3S)-2-amino-3-methyl-pentyl)-(4'-propyl-biphenyl-4-yl)-amide

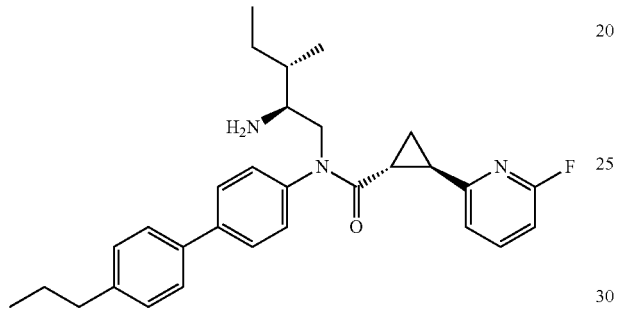

Part A: [(1S,2S)-1-({(4-Bromo-phenyl)-[trans-2-(6-fluoro-pyridin-2-yl)-cyclopropanecarbonyl]-amino}-methyl)-2-methyl-butyl]-carbamic acid tert-butyl ester A mixture of trans-2-(6-fluoro-pyridin-2-yl)-cyclopropanecarboxylic acid (120 mg, 0.55 mmol) in thionyl chloride (2 mL) was heated at reflux for over night. The mixture was concentrated and dried under high vacuum for 3 h. Then the residue was dissolved in DCM (3 mL) and added dropwise to a solution of {(1S,2S)1-[(4-Bromo-phenylamino)-methyl]-2-methyl-butyl}-carbamic acid tert-butyl ester (205 mg, 0.55 mmol) and triethyl amine (153 uL, 1.1 mmol) in DCM (3 mL). The resulting mixture was stirred at rt for overnight. The reaction mixture was concentrated and the residue was subjected to ISCO (12 g column, 0-40% EtOAc in hexane over 25 min.) to give the desired product (235 mg, 80%). MS (MH$^+$ 534 and 536).

Part B: ((1S,2S)-1-{[[Trans-2-(6-fluoro-pyridin-2-yl)-cyclopropanecarbonyl]-(4'-propyl-biphenyl-4-yl)-amino]-methyl}-2-methyl-butyl)-carbamic acid tert-butyl ester A mixture of [(1S,2S)-1-({(4-bromo-phenyl)-[trans-2-(6-fluoro-pyridin-2-yl)-cyclopropanecarbonyl]-amino}-methyl)-2-methyl-butyl]-carbamic acid t-butyl ester (78 mg, 0.146 mmol), arylboronic acid (0.18 mmol), Pd(PPh$_3$)$_2$Cl$_2$ (14 mg, 0.02 mmol) and K$_2$CO$_3$ (38 mg, 0.27 mmol) in CH$_3$CN/H$_2$O (3.5/0.5 mL) was heated in a macrowave at 140° C. for 20 min. The reaction mixture was passed through a short silica pad (EtOAc) and concentrated. The residue was subjected to ISCO (12 g column, 0-50% EtOAc in hexane over 25 min) to give the desired products. MS (MH$^+$ 574).

Part C: Trans-2-(6-fluoro-pyridin-2-yl)-cyclopropanecarboxylic acid ((2S,3S)-2-amino-3-methyl-pentyl)-(4'-propyl-biphenyl-4-yl)-amide A solution of above preparation in DCM (1 mL) was treated with TFA/DCM (1/1 mL) for 1 h. The mixture was concentrated to give the desired products as di-TFA salts. $^1$H NMR (400 MHz, MeOD) δ ppm 7.58-7.73 (m, J=12.9, 8.1, 7.9, 7.9 Hz, 1H), 7.55 (d, J=8.1 Hz, 1H), 7.50 (d, J=7.6 Hz, 1H), 7.39 (dd, J=10.5, 8.2 Hz, 2H), 7.32 (t, J=7.3 Hz, 2H), 7.17 (dd, J=8.2, 3.2 Hz, 2H), 7.09 (ddd, J=13.3, 7.4, 2.0 Hz, 1H), 6.65 (ddd, J=10.7, 8.3, 2.1 Hz, 1H), 4.23 (td, J=14.5, 9.1 Hz, 1H), 3.64 (ddd, J=15.0, 3.2, 3.0 Hz, 1H), 3.28 (ddd, J=12.5, 3.7, 3.5 Hz, 1H), 2.54 (t, J=7.6 Hz, 3H), 1.83-1.97 (m, 1H), 1.62-1.74 (m, 1H), 1.58 (q, J=7.2 Hz, 3H), 1.22-1.40 (m, 2H), 1.13 (ddd, J=14.0, 7.2, 7.1 Hz, 1H), 0.81-0.95 (m, 6H), 0.76 (dt, J=11.6, 7.3 Hz, 3H). LRMS (ESI)=474.3, [(M+H)$^+$, Calcd for $C_{30}H_{37}FN_3O$ 474.6].

Example 15

Trans-2-(6-fluoro-pyridin-2-yl)-cyclopropanecarboxylic acid ((2S,3S)-2-amino-3-methyl-pentyl)-(4'-isopropoxy-biphenyl-4-yl)-amide

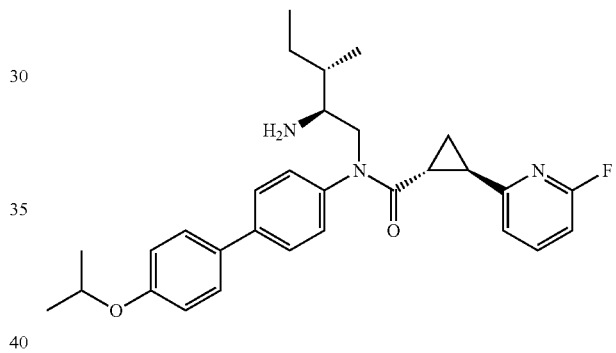

Part A: ((1S,2S)-1-{[[Trans-2-(6-fluoro-pyridin-2-yl)-cyclopropanecarbonyl]-(4'-isopropoxy-biphenyl-4-yl)-amino]-methyl}-2-methyl-butyl)-carbamic acid tert-butyl ester A mixture of [(1S,2S)-1-({(4-bromo-phenyl)-[trans-2-(6-fluoro-pyridin-2-yl)-cyclopropanecarbonyl]-amino}-methyl)-2-methyl-butyl]-carbamic acid t-butyl ester (78 mg, 0.146 mmol), arylboronic acid (0.18 mmol), Pd(PPh$_3$)$_2$Cl$_2$ (14 mg, 0.02 mmol) and K$_2$CO$_3$ (38 mg, 0.27 mmol) in CH$_3$CN/H$_2$O (3.5/0.5 mL) was heated in a macrowave at 140° C. for 20 min. The reaction mixture was passed through a short silica pad (EtOAc) and concentrated. The residue was subjected to ISCO (12 g column, 0-50% EtOAc in hexane over 25 min) to give the desired products. MS (MH$^+$ 590).

Part B: Trans-2-(6-fluoro-pyridin-2-yl)-cyclopropanecarboxylic acid ((2S,3S)-2-amino-3-methyl-pentyl)-(4'-isopropoxy-biphenyl-4-yl)-amide A solution of above preparation in DCM (1 mL) was treated with TFA/DCM (1/1 mL) for 1 h. The mixture was concentrated to give the desired products as di-TFA salts. $^1$H NMR (400 MHz, MeOD) δ ppm 7.6-7.7 (m, J=12.7, 8.2, 7.9, 7.9 Hz, 1H), 7.5 (d, J=8.1 Hz, 1H), 7.5 (d, J=7.8 Hz, 1H), 7.4 (dd, J=10.2, 8.7 Hz, 2H), 7.3 (t, J=7.3 Hz, 2H), 7.1 (ddd, J=12.8, 7.4, 2.3 Hz, 1H), 6.9 (dd, J=8.7, 3.2 Hz, 2H), 6.6 (ddd, J=10.7, 8.2, 2.3 Hz, 1H), 4.5-4.6 (m, J=12.0, 6.0, 6.0, 1.6 Hz, 1H), 4.2 (td, J=14.3, 9.1 Hz, 1H), 3.6 (ddd, J=15.0, 3.3, 3.2 Hz, 1H), 3.3 (dd, J=9.3, 4.0 Hz, 1H), 2.4-2.6 (m, 1H), 1.8-2.0 (m, J=9.3, 9.3, 9.1, 5.6 Hz, 1H), 1.7 (ddd, J=6.7, 4.0, 2.7 Hz, 1H), 1.5-1.6 (m, J=7.2, 5.4, 3.6, 3.6 Hz, 1H), 1.3-1.4 (m, 2H), 1.2 (dd, J=6.1, 1.3 Hz, 6H), 1.1 (ddd, J=13.9, 7.3, 7.1 Hz, 1H), 0.9 (dd, J=6.8, 5.1 Hz, 3H), 0.8 (dt, J=11.4, 7.5 Hz, 3H). LRMS (ESI)=490.3, [(M+H)$^+$, Calcd for $C_{30}H_{32}FN_3O_2$ 489.6].

Example 16

Trans-2-(6-fluoro-pyridin-2-yl)-cyclopropanecarboxylic acid ((2S,3S)-2-amino-3-methyl-pentyl)-(4'-methoxymethyl-biphenyl-4-yl)-amide

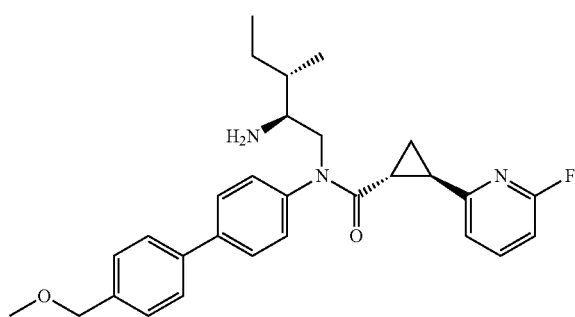 [SMILES: CC[C@H](C)[C@H](N)CN(C(=O)[C@@H]1C[C@H]1c1cccc(F)n1)c1ccc(-c2ccc(COC)cc2)cc1]

Part A: ((1S,2S)-1-{[[Trans-2-(6-fluoro-pyridin-2-yl)-cyclopropanecarbonyl]-(4'-methoxymethyl-biphenyl-4-yl)-amino]-methyl}-2-methyl-butyl)-carbamic acid tert-butyl ester A mixture of [(1S,2S)-1-({(4-bromo-phenyl)-[trans-2-(6-fluoro-pyridin-2-yl)-cyclopropanecarbonyl]-amino}-methyl)-2-methyl-butyl]-carbamic acid t-butyl ester (78 mg, 0.146 mmol), arylboronic acid (0.18 mmol), Pd(PPh$_3$)$_2$Cl$_2$ (14 mg, 0.02 mmol) and K$_2$CO$_3$ (38 mg, 0.27 mmol) in CH$_3$CN/H$_2$O (3.5/0.5 mL) was heated in a microwave at 140° C. for 20 min. The reaction mixture was passed through a short silica pad (EtOAc) and concentrated. The residue was subjected to ISCO (12 g column, 0-50% EtOAc in hexane over 25 min) to give the desired products. MS (MH$^+$ 576).

Part B: Trans-2-(6-fluoro-pyridin-2-yl)-cyclopropanecarboxylic acid ((2S,3S)-2-amino-3-methyl-pentyl)-(4'-methoxymethyl-biphenyl-4-yl)-amide A solution of above preparation in DCM (1 mL) was treated with TFA/DCM (1/1 mL) for 1 h. The mixture was concentrated to give the desired products as di-TFA salts. $^1$H NMR (400 MHz, MeOD) δ ppm 7.6-7.7 (m, J=13.0, 8.1, 7.9, 7.9 Hz, 1H), 7.6 (d, J=8.3 Hz, 1H), 7.5 (d, J=7.8 Hz, 1H), 7.5 (d, J=8.1 Hz, 1H), 7.5 (d, J=8.3 Hz, 1H), 7.3-7.4 (m, 4H), 7.1 (ddd, J=13.3, 7.4, 2.0 Hz, 1H), 6.6 (ddd, J=10.8, 8.4, 2.3 Hz, 1H), 4.4 (s, 2H), 4.2 (ddd, J=15.0, 12.2, 9.0 Hz, 1H), 3.7 (d, J=14.9 Hz, 1H), 3.3 (d, J=1.0 Hz, 3H), 3.2-3.3 (m, 1H), 2.5 (dt, J=19.9, 3.6 Hz, 1H), 1.8-2.0 (m, J=9.4, 9.4, 9.1, 5.4 Hz, 1H), 1.7 (dd, J=4.5, 2.0 Hz, 1H), 1.5-1.6 (m, J=8.9, 8.9, 3.8, 3.5 Hz, 1H), 1.2-1.4 (m, 2H), 1.1 (ddd, J=14.1, 7.3, 7.1 Hz, 1H), 0.9 (dd, J=6.8, 5.1 Hz, 3H), 0.8 (dt, J=11.4, 7.3 Hz, 3H). LRMS (ESI)=476.3, [(M+H)$^+$, Calcd for $C_{29}H_{35}FN_3O_2$ 476.6].

Example 17

(1R,2R)-2-(5-Fluoro-pyridin-2-yl)-cyclopropanecarboxylic acid ((2S,3S)-2-amino-3-methyl-pentyl)-(4-cyclobutylmethoxy-phenyl)-amide

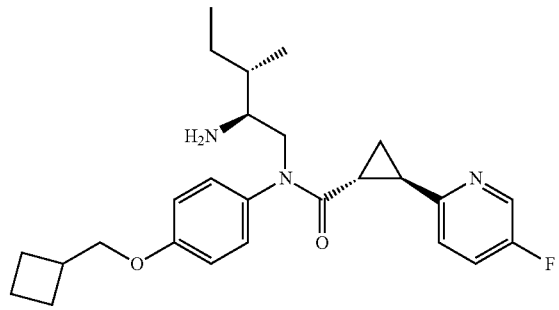 [SMILES: CC[C@H](C)[C@H](N)CN(C(=O)[C@@H]1C[C@H]1c1ccc(F)cn1)c1ccc(OCC2CCC2)cc1]

Part A. ((1S,2S)-1-Formyl-2-methyl-butyl)-carbamic acid tert-butyl ester

To an ice cold solution of Boc-isoleucinol (3.89 g, 17.9 mmol) in DMSO (15 mL) and DCM (200 mL) was added DIEA (9.7 mL, 55.5 mmol), followed by dropwise addition of a solution of Py.SO$_3$ (8.83 g, 55.5 mmol) in DMSO (50 mL, +10 mL to rinse the funnel). The reaction mixture was stirred at rt for 2 h. After removal of the DCM, the residue was diluted with Et$_2$O (400 mL) and washed with H$_2$O (2×100 mL) and brine (150 mL). The aqueous layer was back extracted with Et$_2$O (100 mL). The combined Et$_2$O layer was washed with saturated NaHCO$_3$ (150 mL) and dried (Na$_2$SO$_4$). The solvent was removed to give the titled compound (3.97 g).

Part B. ((1S,2S)-1-{[4-(tert-Butyl-dimethyl-silanyloxy)-phenylamino]-methyl}-2-methyl-butyl)-carbamic acid tert-butyl ester To a solution of ((1S,2S)-1-formyl-2-methyl-butyl)-carbamic acid t-butyl ester (1.3 g, 6 mmol) and 4-tbutyl-dimethylsilanyloxyaniline (1.35 g, 6 mmol) in dichloroethane (40 mL) was added sodium triacetoxyborohydride (2.54 g, 12 mmol) portionwise. After the addition, the resulting mixture was stirred at rt for over night. The reaction mixture was quenched with saturated NaHCO$_3$, and extracted with DCM (4×40 mL). The combined DCM was dried (Na$_2$SO$_4$) and concentrated. The residue was subjected to ISCO (40 g column, 0-50% EtOAc in hexane over 40 min.) to give the titled compound (1.39 g). MS (MH$^+$ 423).

Part C. [(1S,2S)-1-({[4-(tert-Butyl-dimethyl-silanyloxy)-phenyl]-[trans-2-(5-fluoro-pyridin-2-yl)-cyclopropanecarbonyl]-amino}-methyl)-2-methyl-butyl]-carbamic acid tert-butyl ester A mixture of trans-2-(5-fluoro-pyridin-2-yl)-cyclopropanecarboxylic acid HCl salt (217 mg, 1 mmol) in thionyl chloride (2 mL) was heated at reflux for over night. The mixture was concentrated and dried under high vacuum for 3 h. Then the residue was dissolved in DCM (4 mL) and added dropwise to a solution of ((1S,2S)-1-{[4-(t-butyl-dimethyl-silanyloxy)-phenylamino]-methyl}-2-methyl-butyl)-carbamic acid tert-butyl ester (422 mg, 1 mmol) and triethyl amine (409 uL, 3 mmol) in DCM (4 mL). The resulting mixture was stirred at rt for overnight. The reaction mixture was concentrated and the residue was subjected to ISCO (40 g column, 0-40% EtOAc in hexane over 40 min.) to give the titled compound (486 mg, 83%). MS (MH+ 586).

Chiral HPLC separated the two diasteromers Column. ChiralPak AD-H 20 mm×250 mm, 30% Ethanol in hexane isocratic, retention time: 10.36 min and 12.22 min.] to give:
[(1S,2S)-1-({[4-(tert-Butyl-dimethyl-silanyloxy)-phenyl]-[(1R,2R)-2-(5-fluoro-pyridin-2-yl)-cyclopropanecarbonyl]-amino}-methyl)-2-methyl-butyl]-carbamic acid tert-butyl ester
[(1S,2S)-1-({[4-(tert-Butyl-dimethyl-silanyloxy)-phenyl]-[(1S,2S)-2-(5-fluoro-pyridin-2-yl)-cyclopropanecarbonyl]-amino}-methyl)-2-methyl-butyl]-carbamic acid tert-butyl ester Part D. ((1S,2S)-1-{[[(1R,2R)-2-(5-Fluoro-pyridin-2-yl)-cyclopropanecarbonyl]-(4-hydroxy-phenyl)-amino]-methyl}-2-methyl-butyl)-carbamic acid tert-butyl ester To a solution of [(1S,2S)-1-({[4-(t-butyl-dimethyl-silanyloxy)-phenyl]-[(1R,2R)-2-(5-fluoro-pyridin-2-yl)-cyclopropanecarbonyl]-amino}-methyl)-2-methyl-butyl]-carbamic acid tert-butyl ester (190 mg) in THF (3 mL) was added TBAF in THF (1M, 1 mL) the resulting solution was stirred at rt for 2 h. The reaction mixture was diluted with EtOAc (30 mL) and washed with H$_2$O (2×15 mL) and brine (15 mL). The EtOAc layer was dried (Na$_2$SO$_4$) and concentrated to give the titled compound (102 mg). MS (MH+ 472).

Part E. [(1S,2S)-1-({(4-Cyclobutylmethoxy-phenyl)-[(1R,2R)-2-(5-fluoro-pyridin-2-yl)-cyclopropanecarbonyl]-amino}-methyl)-2-methyl-butyl]-carbamic acid tert-butyl ester A mixture of ((1S,2S)-1-{[[(1R,2R)-2-(5-fluoro-pyridin-2-yl)-cyclopropanecarbonyl]-(4-hydroxy-phenyl)-amino]-methyl}-2-methyl-butyl)-carbamic acid tert-butyl ester (51 mg, 0.11 mmol), K$_2$CO$_3$ (69 mg, 0.5 mmol) and cyclobutylmethyl bromide (22 mg, 0.15 mmol) in DMF was stirred at 55° C. for over night. After cool to rt, the mixture was filtered through a silica pad (EtOAc). The filtrate was concentrated and the residue was subjected to ISCO (12 g column, 0-40% EtOAc in hexane over 25 min) to give the titled compound (53 mg). MS (MH+ 540).

Part F. (1R,2R)-2-(5-Fluoro-pyridin-2-yl)-cyclopropanecarboxylic acid ((2S,3S)-2-amino-3-methyl-pentyl)-(4-cyclobutylmethoxy-phenyl)-amide A solution of [(1S,2S)-1-({(4-cyclobutylmethoxy-phenyl)-[(1R,2R)-2-(5-fluoro-pyridin-2-yl)-cyclopropanecarbonyl]-amino}-methyl)-2-methyl-butyl]-carbamic acid tert-butyl ester (53 mg) in DCM (1 mL) was treated with TFA/DCM (1/1 mL) for 1 h. The mixture was concentrated to give the titled compound as di-TFA salts (60.7 mg). $^1$H NMR (400 MHz, MeOD) δ ppm 8.2 (d, J=3.0 Hz, 1H), 7.5 (td, J=8.5, 2.9 Hz, 1H), 7.3 (dd, J=8.8, 4.3 Hz, 1H), 7.3 (d, J=8.1 Hz, 2H), 6.9 (d, J=8.3 Hz, 2H), 4.3 (dd, J=14.9, 8.8 Hz, 1H), 3.9 (dd, J=6.6, 2.3 Hz, 2H), 3.6 (dd, J=14.9, 2.8 Hz, 1H), 3.3-3.4 (m, 1H), 2.8 (dt, J=14.6, 7.2 Hz, 1H), 2.6 (dd, J=6.3, 2.5 Hz, 1H), 2.1 (td, J=8.5, 5.6 Hz, 2H), 1.8-2.1 (m, 5H), 1.8 (ddd, J=7.7, 5.9, 1.5 Hz, 1H), 1.7 (ddd, J=9.0, 5.4, 3.8 Hz, 1H), 1.4 (ddd, J=8.5, 6.0, 3.9 Hz, 1H), 1.4 (dd, J=7.5, 5.7 Hz, 1H), 1.2 (dd, J=15.5, 5.4 Hz, 1H), 1.0 (d, J=6.8 Hz, 3H), 0.9 (t, 3H). LRMS (ESI)= 440.3, [(M+H)+, Calcd for C$_{26}$H$_{35}$FN$_3$O$_2$ 439.6].

Example 18

Trans-2-pyrazin-2-yl-cyclopropanecarboxylic acid ((2R,3R)-2-amino-3-methoxy-butyl)-(4'-propyl-biphenyl-4-yl)-amide

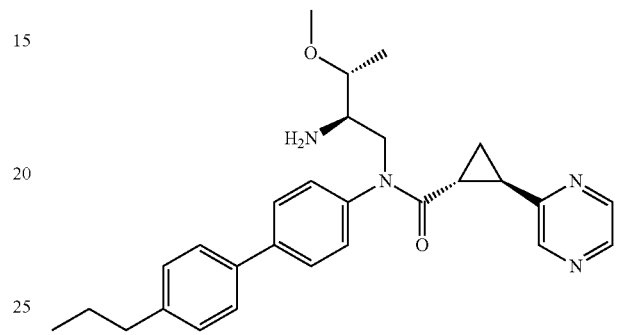

Part A. ((1R,2R)-1-Hydroxymethyl-2-methoxy-propyl)-carbamic acid tert-butyl ester To a cold solution (−15° C.) of BocThr(Me)OH (5.14 g, 22 mmol) in dichloroethane (22 mL) were successively added N-methyl morpholine (2.44 mL, 22 mmol) and isobutyl chloroformate (2.99 mL, 22 mmol). After one min, the precipitate was filtered and washed with dichloroethane (5×4 mL). The filtrate and washings were combined in a large three neck flask in an ice-salt bath. A solution of NaBH$_4$ (1.26 g, 33 mmol) in H$_2$O (11 mL) was added at once, proceeding a strong evolution of gas, followed by H$_2$O (500 mL). The mixture was then extracted with EtOAc (5×150 mL). The combined EtOAc was dried (Na$_2$SO$_4$) and concentrated to give the titled compound (5 g). MS (MH+ 220).

Part B. ((1S,2R)-1-Formyl-2-methoxy-propyl)-carbamic acid tert-butyl ester

To an ice cold solution of ((1R,2R)-1-hydroxymethyl-2-methoxy-propyl)-carbamic acid t-butyl ester (5 g, 22 mmol) in DMSO (20 mL) and DCM (250 mL) was added DIEA (12 mL, 69 mmol), followed by dropwise addition of a solution of Py.SO$_3$ (11 g, 69 mmol) in DMSO (50 mL, +20 mL to rinse the funnel). The reaction mixture was stirred at rt for 5 h. After removal of the DCM, the residue was diluted with Et$_2$O (400 mL) and washed with H$_2$O (2×100 mL) and brine (150 mL). The aqueous layer was back extracted with Et$_2$O (100 mL). The combined Et$_2$O layer was washed with saturated NaHCO$_3$ (150 mL) and dried (Na$_2$SO$_4$). The solvent was removed to give the titled compound. MS (MH+ 218).

Part C. {(1R,2R)-1-[(4-Bromo-phenylamino)-methyl]-2-methoxy-propyl}-carbamic acid tert-butyl ester To a solution of ((1S,2R)-1-formyl-2-methoxy-propyl)-carbamic acid t-butyl ester (1.92 g, 8.8 mmol) and 4-bromoaniline (1.51 g, 8.8 mmol) in dichloroethane (50 mL) was added sodium triacetoxyborohydride (3.73 g, 17.6 mmol) portionwise. After the addition, the resulting mixture was stirred at rt for over night. The reaction mixture was quenched with saturated NaHCO$_3$, and extracted with DCM (4×40 mL). The combined DCM was dried (Na$_2$SO$_4$) and concentrated. The residue was subjected to ISCO (120 g column, 0-40% EtOAc in hexane over 100 min.) to give the titled compound (610 mg). MS (MH$^+$ 373 and 375).

Part D. ((1R,2R)-1-{[(4-Bromo-phenyl)-(trans-2-pyrazin-2-yl)-cyclopropanecarbonyl)-amino]-methyl}-2-methoxy-propyl)-carbamic acid tert-butyl ester A mixture of trans-2-pyrazin-2-yl-cyclopropanecarboxylic acid HCl salt (160 mg, 0.8 mmol) in thionyl chloride (2 mL) was heated at reflux for 3 h. The mixture was concentrated and dried under high vacuum for overnight. Then the residue was suspended in DCM (2 mL) and to it was added a solution of {(1R,2R)-1-[(4-Bromo-phenylamino)-methyl]-2-methoxy-propyl}-carbamic acid t-butyl ester (300 mg, 0.8 mmol) and triethyl amine (223 uL, 1.6 mmol) in DCM (2 mL, +1 mL for washing). The resulting mixture was stirred at rt for overnight. The reaction mixture was concentrated and the residue was subjected to ISCO (40 g column, 0-60% EtOAc in hexane over 40 min.) to give the titled compound (340 mg, 82%). MS (MH$^+$ 519 and 521).

Part E. ((1R,2R)-2-Methoxy-1-{[(4'-propyl-biphenyl-4-yl)-(trans-2-pyrazin-2-yl-cyclopropanecarbonyl)-amino]-methyl}-propyl)-carbamic acid tert butyl ester A mixture of ((1R,2R)-1-{[(4-bromo-phenyl)-(trans-2-pyrazin-2-yl)-cyclopropanecarbonyl)-amino]-methyl}-2-methoxy-propyl)-carbamic acid tert-butyl ester (85 mg, 0.16 mmol), arylboronic acid (31 mg, 0.19 mmol), Pd(PPh$_3$)$_2$Cl$_2$ (14 mg, 0.02 mmol) and K$_2$CO$_3$ (42 mg, 0.3 mmol) in CH$_3$CN/H$_2$O (3.5/0.5 mL) was heated in a macrowave at 140° C. for 20 min. The reaction mixture was passed through a short silica pad (EtOAc) and concentrated. The residue was subjected to ISCO (12 g column, 0-50% EtOAc in hexane over 25 min) to give the titled compound (64 mg). MS (MH$^+$ 559).

Part F. Trans-2-pyrazin-2-yl-cyclopropanecarboxylic acid ((2R,3R)-2-amino-3-methoxy-butyl)-(4'-propyl-biphenyl-4-yl)-amide A solution of ((1R,2R)-2-methoxy-1-{[(4'-propyl-biphenyl-4-yl)-(trans-2-pyrazin-2-yl-cyclopropanecarbonyl)-amino]-methyl}-propyl)-carbamic acid tert butyl ester (55 mg) in DCM (1 mL) was treated with TFA/DCM (2/2 mL) for 1 h. The mixture was concentrated to give the titled compound as di-TFA salts (65.5 mg). $^1$H NMR (400 MHz, MeOD) δ ppm 8.5 (d, J=5.3 Hz, 1H), 8.1-8.2 (m, 2H), 7.5 (t, J=8.0 Hz, 2H), 7.4 (dd, J=8.3, 4.5 Hz, 2H), 7.3 (dd, J=8.2, 3.4 Hz, 2H), 7.2 (dd, J=8.1, 1.5 Hz, 2H), 4.2 (ddd, J=14.8, 8.5, 8.3 Hz, 1H), 3.8 (ddd, J=14.7, 7.9, 4.2 Hz, 1H), 3.4 (qd, J=6.1, 5.9 Hz, 1H), 3.2 (s, 3H), 3.2-3.2 (m, 1H), 2.6 (dddd, J=14.8, 6.1, 5.7, 4.2 Hz, 1H), 2.5 (t, J=7.6 Hz, 2H), 2.0 (q, J=8.3 Hz, 1H), 1.7 (dddd, J=8.9, 7.1, 5.6, 3.7 Hz, 1H), 1.6 (d, J=7.6 Hz, 2H), 1.3-1.4 (m, J=8.5, 5.8, 2.9, 2.9 Hz, 1H), 1.1 (dd, J=6.1, 3.0 Hz, 3H), 0.9 (t, J=7.3 Hz, 3H). LRMS (ESI)=459.3, [(M+H)$^+$, Calcd for C$_{28}$H$_{35}$N$_4$O$_2$ 459.6].

Example 19

(1S,2S)-2-(6-Fluoro-pyridin-2-yl)-cyclopropanecarboxylic acid ((2S,3S)-2-amino-3-methyl-pentyl)-(4-pent-1-ynyl-phenyl)-amide 2TFA

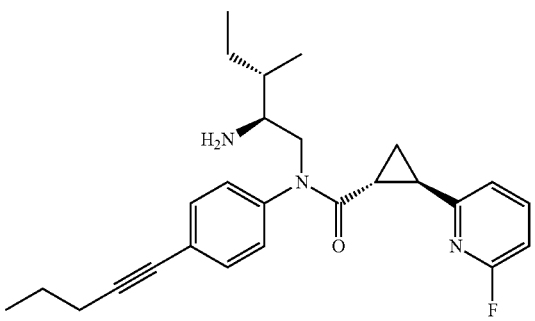 [SMILES: CCCC#Cc1ccc(N(C[C@@H](N)[C@@H](C)CC)C(=O)[C@@H]2C[C@H]2c2cccc(F)n2)cc1]

Part A. [(1S,2S)-1-({(4-Bromo-phenyl)-[trans-2-(6-fluoro-pyridin-2-yl)-cyclopropanecarbonyl]-amino}-methyl)-2-methyl-butyl]-carbamic acid t-butyl ester Trans-2-(6-fluoro-pyridin-2-yl)-cyclopropanecarboxylic acid (0.150 g, 0.83 mmol) was dissolved in thionyl chloride (2 mL), which was stirred and heated at 60° C. for 1.5 hrs. The excessive solvent was removed on ratovapor and dried under high vacuum for 2 hrs to give the corresponding acid chloride. In a separated 50 mL round-bottom flask was charged with {(1S,2S)-1-[(4-bromo-phenylamino)-methyl]-2-methyl-butyl}-carbamic acid t-butyl ester (0.308 g, 0.83 mmol), dichloromethane (8 mL) and triethylamine (0.46 mL, 3.32 mmol) in an ice cold bath under nitrogen. The acid chloride mentioned above, in dichloromethane (2 mL) was added into the reaction mixture dropwise. The final reaction mixture was stirred for 2 hrs at room temperature. The finished reaction was quenched with water. The organic phase was washed with brine (3×10 mL), dried over MgSO$_4$, filtrated, concentrated in vacuum and purified via column chromatography on silica gel with a gradient of 0%-100% of ethyl acetate in hexane to give clear oil of diasteromers of the title compound (0.443 g, 46% yield): LCMS (ESI) m/e 534.0/536.0 [(M+H)$^+$, calcd for C$_{26}$H$_{34}$BrFN$_3$O$_3$ 535.5].

Part B. ((1S,2S)-1-{[[(1S,2S)-2-(6-Fluoro-pyridin-2-yl)-cyclopropanecarbonyl]-(4-pent-1-ynyl-phenyl)-amino]-methyl}-2-methyl-butyl)-carbamic acid t-butyl ester

[(1S,2S)-1-({(4-Bromo-phenyl)-[trans-2-(6-fluoro-pyridin-2-yl)-cyclopropanecarbonyl]-amino}-methyl)-2-methyl-butyl]-carbamic acid t-butyl ester (0.068 g, 0.127 mmol), 1-pentyne (0.05 mL, 0.509 mmol), PdCl$_2$(PPh$_3$)$_2$ (0.017 g, 0.025 mmol) and 1N TBAF in THF (0.76 mL, 0.762 mmol) were mixed in THF (1 mL) in sealed microwave flask. The reaction mixture was heated at 90° C. at normal setting for 30 minutes. The reaction mixture was quenched with brine. The aqueous phase was extracted by ethyl acetate (3×7 mL). The combined organic layers were washed brine and dried over MgSO$_4$, filtered and concentrated to give yellow oil. The crude product was purified via column chromatography on silica gel with a gradient of 0%-50% of ethyl acetate in hexanes to afford the title product as yellow oil (0.066 g, 99% yield): $^1$H NMR (400 MHz, CDCl$_3$) δ ppm 7.32 (m, 4H), 6.86 (m, 3H), 6.42 (m, 1H), 4.76 (d, J=9.1 Hz, 1H), 4.11 (m, 1H), 3.48 (m, 1H), 2.95 (td, J=13.1, 3.8 Hz, 1H), 2.42 (m, 1H), 2.16 (td, J=7.0, 3.4 Hz, 2H), 1.67 (m, 1H), 1.40 (m, 4H), 1.22 (m, 11H), 0.84 (m, 3H), 0.63 (m, 6H); LCMS (ESI) m/e 522.4 [(M+H), calcd for C$_{31}$H$_{41}$FN$_3$O$_3$ 522.7].

Part C. (1S,2S)-2-(6-Fluoro-pyridin-2-yl)-cyclopropanecarboxylic acid ((2S,3S)-2-amino-3-methylpentyl)-(4-pent-1-ynyl-phenyl)-amide 2TFA ((1S,2S)-1-{[[(1S,2S)-2-(6-Fluoro-pyridin-2-yl)-cyclopropanecarbonyl]-(4-pent-1-ynyl-phenyl)-amino]-methyl}-2-methyl-butyl)-carbamic acid t-butyl ester (0.0657 g, 0.126 mmol), trifluoroacetic acid (1 mL) and dichloromethane (2 mL) were mixed at 0° C., then stirred at room temperature for 1 hr. The excessive solvent was removed in vacuum. The residue was purified by preparatory HPLC to give a white solid (0.0277 g, 34%): $^1$H NMR (400 MHz, MeOD) δ ppm 7.66 (m, 1H), 7.24 (m, 4H), 7.07 (td, J=7.1, 2.3 Hz, 1H), 6.66 (m, 1H), 4.16 (m, 1H), 3.58 (m, 1H), 3.21 (dt, J=3.3, 1.6 Hz, 1H), 2.47 (br. s., 1H), 2.29 (td, J=7.0, 3.2 Hz, 2H), 1.81 (dd, J=5.3, 3.5 Hz, 1H), 1.62 (m, 1H), 1.53 (m, 3H), 1.29 (m, 2H), 1.10 (m, 1H), 0.95 (td, J=7.3, 2.5 Hz, 3H), 0.86 (dd, J=7.1, 4.8 Hz, 3H), 0.73 (m, 3H); LCMS (ESI) m/e 422.3 [(M+H)$^+$, calcd for C$_{26}$H$_{33}$FN$_3$O 422.6].

Example 20

Trans-2-(5-Fluoro-pyridin-2-yl)-cyclopropanecarboxylic acid (2S,3S)-2-amino-3-methyl-pentyl)-(6-cyclopropyl-naphthalen-2-yl)-amide

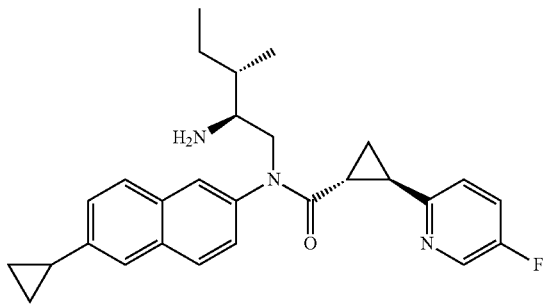 [SMILES: CC[C@H](C)[C@H](N)CN(C(=O)[C@@H]1C[C@H]1c1ccc(F)cn1)c1ccc2cc(C3CC3)ccc2c1]

Part A. ((1S,2S)-1-Formyl-2-methyl-butyl)-carbamic acid tert-butyl ester

To a suspension of N-Boc-L-isoleucinol (5 g, 23 mmol) in dichloromethane (250 mL) and DMSO (50 mL) at 0° C. was added TEA (10 mL, 73 mmol) followed by slow addition of the solution of sulfur trioxide pyridine complex (11 mL, 69 mmol) in DMSO (50 mL) via syringe. The reaction mixture was concentrated and was diluted with ether (200 mL). The layers were separated and the aqueous layer was extracted with ethyl acetate (3×200 mL), which was then washed with brine (150 mL), water (150 mL) and NaHCO$_3$ (150 mL) sequentially. The organic layers were dried over MgSO$_4$, filtered and concentrated. The residue was dried on pump to afford ((1S,2S)-1-formyl-2-methyl-butyl)-carbamic acid tert-butyl ester (4.47 g, 90% yield) as light-yellow clear liquid.

Part B. {(1S,2S)-1-[(6-Bromo-naphthalen-2-ylamino)-methyl]-2-methyl-butyl}-carbamic acid tert-butyl ester ((1S,2S)-1-Formyl-2-methyl-butyl)-carbamic acid tert-butyl ester (1.62 g, 7.5 mmol), and 6-bromo-naphthalen-2-ylamine (1.11 g, 5.0 mmol) were combined in DCE (10 mL). After stirring 5 min, NaBH(OAc)$_3$ (2.33 g, 11 mmol) was added. The whole mixture was then stirred at r.t. for 18 h. The reaction mixture was transferred to a separatory funnel containing water (50 mL). The aqueous layer was extracted with DCM (3×50 mL). The combined organic layers were washed with brine (50 mL), dried over MgSO$_4$, filtered and concentrated. The residue was purified via column chromatography on silica gel (10% ethyl acetate in hexanes) to afford {(1S,2S)-1-[(6-bromo-naphthalen-2-ylamino)-methyl]-2-methyl-butyl}-carbamic acid tert-butyl ester (1.78 g, 85% yield) as an off-white solid. LC/MS (ESI) m/e 423.2 [(M+H)$^+$, calcd for C$_{21}$H$_{29}$BrN$_2$O$_2$ 421.4].

Part C. {(1S,2S)-1-[(6-Cyclopropyl-naphthalen-2-ylamino)-methyl]-2-methyl-butyl}-carbamic acid tert-butyl ester {(1S,2S)-1-[(6-Bromo-naphthalen-2-ylamino)-methyl]-2-methyl-butyl}-carbamic acid tert-butyl ester (210 mg, 0.5 mmol), 2-cyclopropyl-4,4,5,5-tetramethyl-1,3,2-dioxaborolane (336 mg, 2.0 mmol), Pd(dppf)$_2$Cl$_2$ (82 mg, 0.1 mmol), K$_3$PO$_4$ (320 mg, 1.5 mmol) was combined in the mixture of DME (2.4 mL) and water (0.6 mL). The reaction mixture was heated at 130° C. for 10 mins under Microwave condition. The reaction mixture was cooled to r.t. and was quenched by the slow addition of 1N NaOH solution (15 mL). The reaction mixture was transferred to a separatory funnel containing water (20 mL). The aqueous layer was extracted with DCM (3×50 mL). The combined organic layers were washed with brine (50 mL), dried over MgSO$_4$, filtered and concentrated. The residue was purified on silica gel (7%→17% ethyl acetate in hexanes) to afford {(1S,2S)-1-[(6-cyclopropyl-naphthalen-2-ylamino)-methyl]-2-methyl-butyl}-carbamic acid tert-butyl ester (107 mg, 60% yield) as a light brown solid: LC/MS (ESI) m/e 383.3 [(M+H)$^+$, calcd for C$_{24}$H$_{34}$N$_2$O$_2$ 382.6].

Part D. [(1S,2S)-1-({(6-Cyclopropyl-naphthalen-2-yl)-[trans-2-(5-fluoro-pyridin-2-yl)-cyclopropanecarbonyl]-amino}-methyl)-2-methyl-butyl]-carbamic acid tert-butyl ester Trans-2-(5-fluoro-pyridin-2-yl)-cyclopropanecarboxylic acid (35 mg, 0.16 mmol) was dissolved in SOCl$_2$ (2 mL) and was heated at 65° C. for 3 hrs. Removal of SOCl$_2$ carefully under pump and dried the residue under high vacuum for 3 hrs. To a solution of {(1S,2S)-1-[(6-cyclopropyl-naphthalen-2-ylamino)-methyl]-2-methyl-butyl}-carbamic acid tert-butyl ester (55 mg, 0.14 mmol) and triethylamine (0.084 mL, 0.6 mmol) in DCM (3 mL) at 0° C. was added freshly made trans-2-(5-fluoro-pyridin-2-yl)-cyclopropanecarbonyl chloride in DCM (2 mL) slowly. The reaction mixture was then stirred at r.t. for 18 hrs. The reaction mixture was transferred to a separatory funnel containing water (20 mL). The aqueous layer was extracted with DCM (3×20 mL). The combined organic layers were washed with brine (20 mL), dried over MgSO₄, filtered and concentrated. The residue was purified by Prep HPLC to afford [(1S,2S)-1-({(6-cyclopropyl-naphthalen-2-yl)-[trans-2-(5-fluoro-pyridin-2-yl)-cyclopropanecarbonyl]-amino}-methyl)-2-methyl-butyl]-carbamic acid tert-butyl ester as a solid: LC/MS (ESI) m/e 546 [(M+H)⁺, calcd for $C_{33}H_{40}FN_3O_3$ 545.7].

Part E. Trans-2-(5-Fluoro-pyridin-2-yl)-cyclopropanecarboxylic acid ((2S,3S)-2-amino-3-methyl-pentyl)-(6-cyclopropyl-naphthalen-2-yl)-amide.TFA A solution of [(1S,2S)-1-({(6-cyclopropyl-naphthalen-2-yl)-[trans-2-(5-fluoro-pyridin-2-yl)-cyclopropanecarbonyl]-amino}-methyl)-2-methyl-butyl]-carbamic acid tert-butyl ester in DCM (1.5 mL) was added TFA (0.25 mL) and was stirred at room temperature for 40 mins. The reaction mixture was concentrated, dried under vacuum to afford trans-2-(5-fluoro-pyridin-2-yl)-cyclopropanecarboxylic acid ((2S,3S)-2-amino-3-methyl-pentyl)-(6-cyclopropyl-naphthalen-2-yl)-amide.TFA (14.2 mg, 18% yield in 2 steps) as a tan solid: ¹H NMR (400 MHz, MeOD) δ 7.90-7.93 (d, J=12 Hz, 1H), 7.53-7.78 (m, 4H), 7.25-7.32 (m, 2H), 7.10-7.31 (m, 2H), 4.19-4.30 (m, 1H), 3.67-3.75 (m, 1H), 3.20-3.30 (m, 1H), 2.49-2.59 (m, 1H), 1.90-2.01 (m, 1H), 1.75-1.84 (m, 1H), 1.55-1.67 (m, 2H), 1.19-1.31 (m, 2H), 1.07-1.12 (m, 1H), 0.90-0.97 (m, 2H), 0.80-0.90 (m, 3H), 0.25-0.75 (m, 5H); LC/MS (ESI) m/e 446.2 [(M+H)⁺, calcd for $C_{28}H_{33}FN_3O$ 446.6].

Biological Activity

Materials:
96 well GTPγS assay plates were purchased from Perkin Elmer. Wheat Germ Agglutinin PVT SPA beads and ³⁵S-GTPγS were purchased from Amersham GDP, GTPγS and all buffer reagents were from Sigma. 384 well white NBS plates were purchased from corning. Pertussis toxin was purchased from Calbiochem. All cell culture reagents were purchased from Invitrogen. Forskolin was purchased from Sigma. The cAMP HTRF kit was purchased from Cisbio International.
Methods:
GTPγS Assay
The GTPγS assay buffer consisted of 10 mM MgCl₂, 180 mM NaCl, 200 uM GDP, 0.167 mg/ml DTT, 1 mM EGTA and 20 mM HEPES pH7.4. This buffer was used for dilution of membranes, beads, and ³⁵S GTPγS components. To each well of the 96 well assay plate 48 ul assay buffer, 2 ul of 100× compound, 50 ul membrane solution (0.2 ug/ul), 50 ul ³⁵S GTPγS solution (0.8 nM) and 50 ul of SPA beads (10 mg/ml). Non-specific binding was determined by the addition of cold GTPγS to control wells. The plates were sealed with clear sealing tape and incubated at room temperature for 1 hour. GTPγS activity was detected using a Wallac Micro-Beta Trilux liquid scintillation counter. Non-specific binding was determined using 10 uM cold GTPγS.
cAmp HTRF Assay
The cAMP HTRF assay is modified from the Cisbio International kit procedure 62AM4PEJ. Assay plates were prepared by stamping 0.1 ul of 100× compound stock solutions diluted in DMSO or DMSO alone into 384 well NBS plates. The cAMP HTRF assay was performed using cells in suspension. The cAMP HTRF assay buffer consisted of Hank's Balanced Salt Solution (HBSS), 2 mM CaCl₂, 5 mM MgCl₂, 20 mM HEPES and 1 mM 3-isobutyl-1-methylxanthine (IBMX) (added fresh at the time of assay). For pertussis toxin treatment pertussis toxin (100 ng/ml) was added to culture medium for 16 hours prior to assay. Confluent cells were disrupted with cell dissociation buffer count cells then centrifuged at 1000×g for 5 minutes. The cell pellet was resuspended in assay buffer alone for basal cAMP measurements or with 0.75 uM forskolin (added immediately prior to addition to wells) for addition to all other wells. Using a Multidrop 384 (Lab systems) 10 ul of cell suspension was added to each well containing compound or DMSO. The plates were incubated at room temperature for 30 minutes covered. During this time the cAMP standard curve was prepared as per manufacturer's instruction. At the end of the incubation 10 ul of anti-cAMP cryptate and 10 ul cAMP-XL, diluted in manufacturer's lysis buffer, were added to each well. The plated were incubated at room temperature for 60 minutes covered then read on an Envision plate reader (Perkin Elmer) and the 665 nm/620 nm fluorescence ratio determined Fluorescence ratio values were converted to molar cAMP concentrations from the standard curve using the GraphPad Prism program.

Table 2 shows EC50 values for select compounds of the present disclosure: All compounds marked "X" had an EC50 of between 3 nM and 20 nM.

TABLE 2

| Example Number | Range (EC50) |
|---|---|
| 1 | X |
| 2 | X |
| 3 | 3 nM |
| 4 | X |
| 5 | X |
| 6 | X |
| 7 | X |
| 8 | X |
| 9 | X |
| 10 | X |
| 11 | X |
| 12 | 20 nM |
| 13 | X |
| 14 | X |
| 15 | 8 nM |
| 16 | X |
| 17 | X |
| 18 | X |
| 19 | X |
| 20 | X |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:
1. A compound of formula (II)

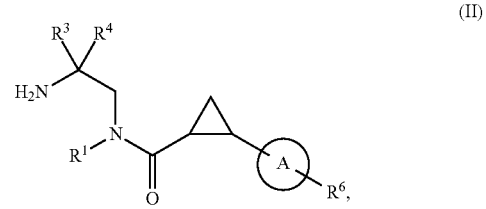

or a pharmaceutically acceptable salt thereof, wherein

A is selected from pyrazinyl and pyridinyl;

R[1] is selected from:

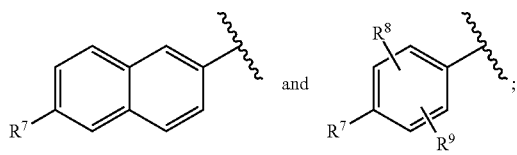

and wherein "⸾" denotes the point of attachment to the parent molecular moiety;

R[3] is selected from $C_4$ alkyl and $C_1$ alkoxy-$C_2$ alkyl;

R[4] is hydrogen; or

R[3] and R[4], together with the carbon atom to which they are attached, form a carbonyl group, or form a ring selected from $C_5$ cycloalkyl and tetrahydropyranyl;

R[6] is selected from hydrogen and halo; and

R[7] is selected from $C_5$ alkynyl;

$C_3$ cycloalkyl;

$C_4$ cycloalkyl-$C_1$ alkoxy; and phenyl optionally substituted with one substituent selected from $C_3$ alkoxy, $C_1$ alkoxy-$C_1$ alkyl, $C_3$ alkyl, and $C_2$ alkynyl, provided that when the phenyl is substituted the substituent is in the para position on the phenyl ring;

R[8] is selected from hydrogen; $C_1$-$C_3$ alkyl; and halo; and

R[9] is selected from hydrogen; $C_1$-$C_3$ alkyl; and halo.

2. A compound selected from

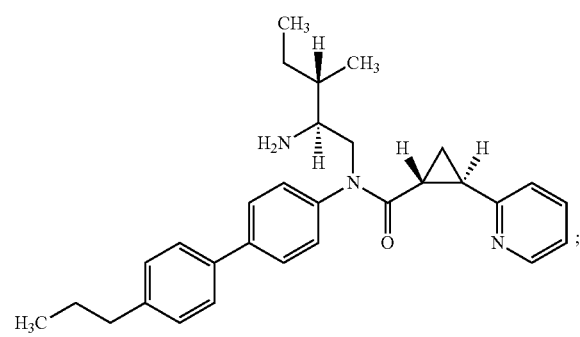

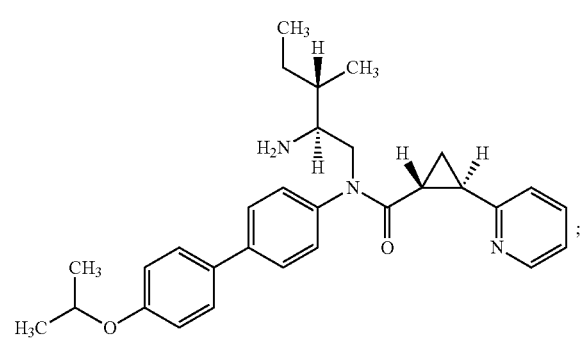

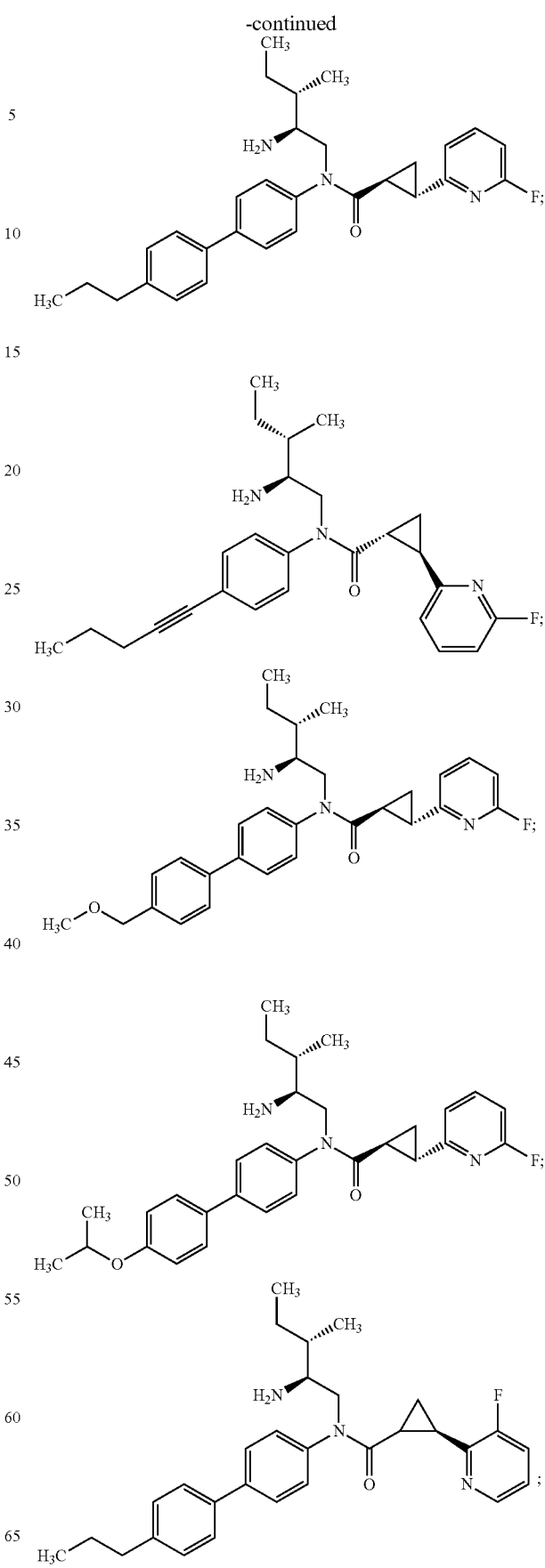

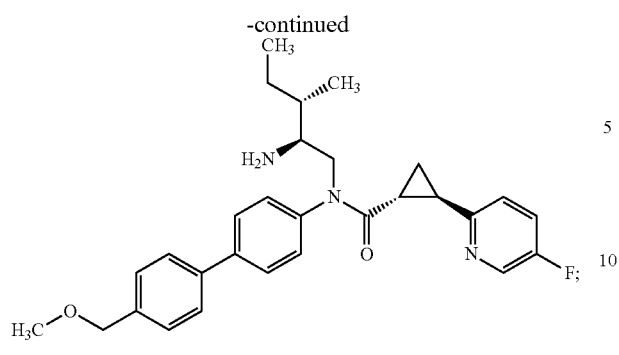
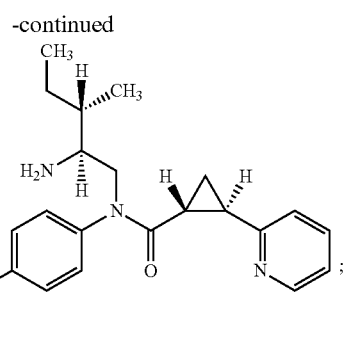
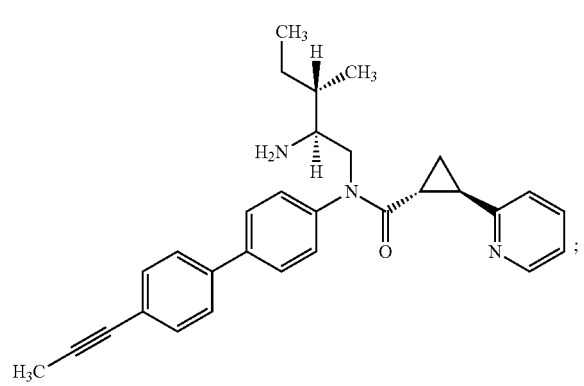
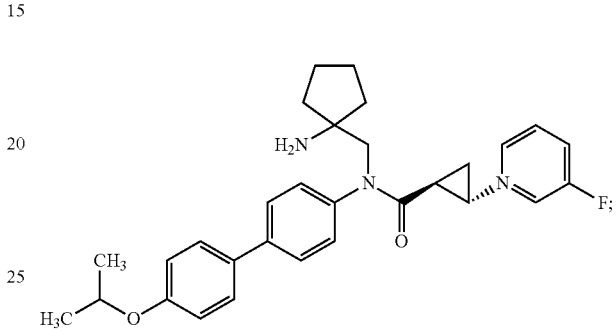
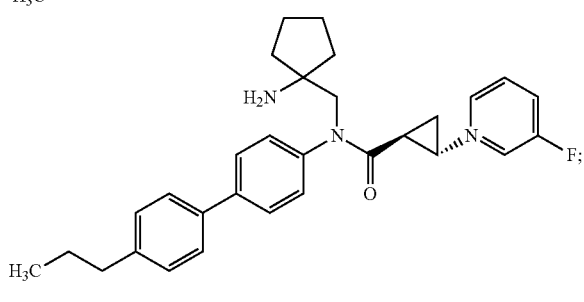
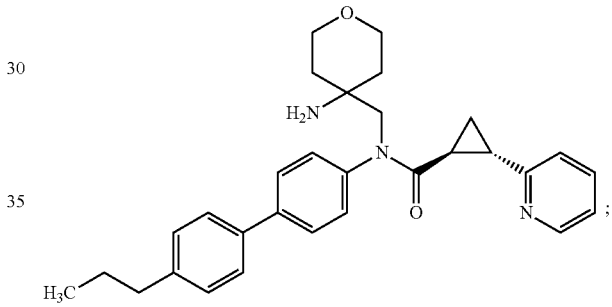
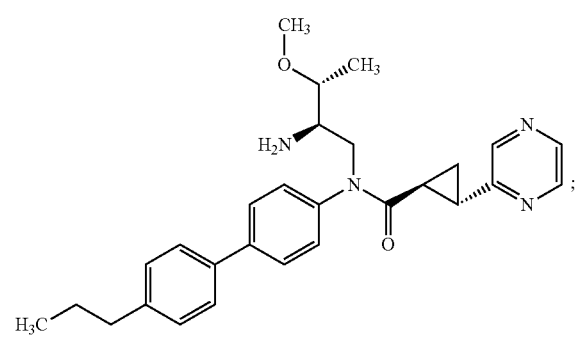
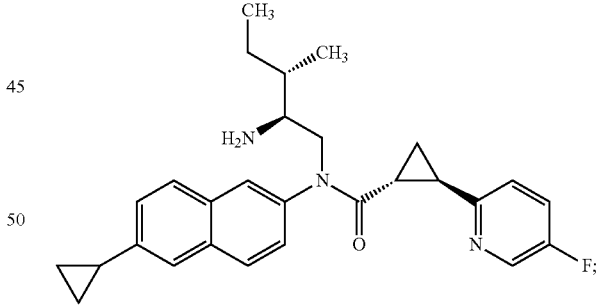
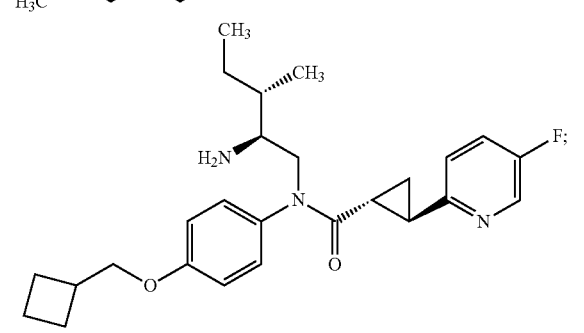
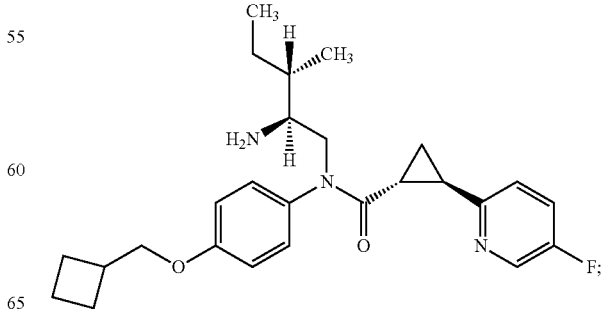

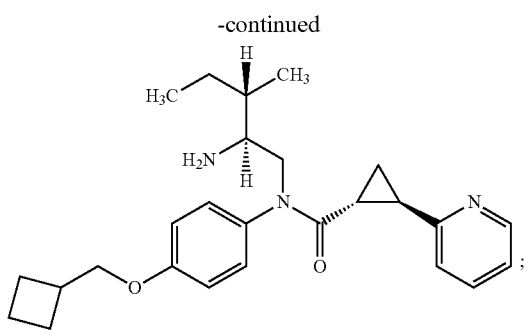

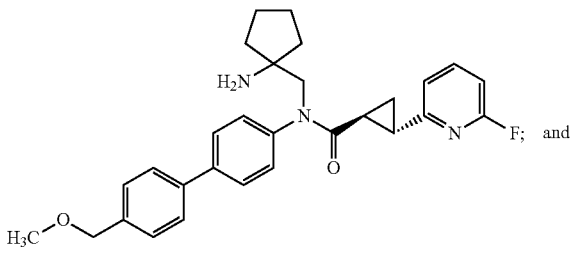

or a pharmaceutically acceptable salt thereof.

3. A composition comprising a compound of claim 1, or a pharmaceutically acceptable salt thereof, and a pharmaceutically acceptable carrier.

4. A method of modulating G protein-coupled receptor 88 in a mammal, comprising administering to the mammal a therapeutically effective amount of a compound of claim 1, or a pharmaceutically acceptable salt thereof.

5. The method of claim 4 wherein the mammal is a human.

6. The method of claim 4 wherein the G protein-coupled receptor 88 is modulated in order to treat a neurological disorder.

7. The method of claim 6 wherein the G protein-coupled receptor 88 is modulated in order to treat a neurological disorder wherein the neurological disorder is selected from psychosis, cognitive deficits in schizophrenia, affective disorders, attention deficit hyperactivity disorders, bipolar disorder, drug addiction, Parkinson's disease, and Alzheimer's disease.

* * * * *

UNITED STATES PATENT AND TRADEMARK OFFICE
CERTIFICATE OF CORRECTION

PATENT NO. : 8,426,414 B2
APPLICATION NO. : 12/897004
DATED : April 23, 2013
INVENTOR(S) : Yingzhi Bi et al.

It is certified that error appears in the above-identified patent and that said Letters Patent is hereby corrected as shown below:

On the Title Page, Col. 1, line 7, (75) Inventors,
Delete "Gullford," and insert -- Guilford, --, therefor.

In the Claims:
In Claim 2, col. 53, lines 30-35, delete

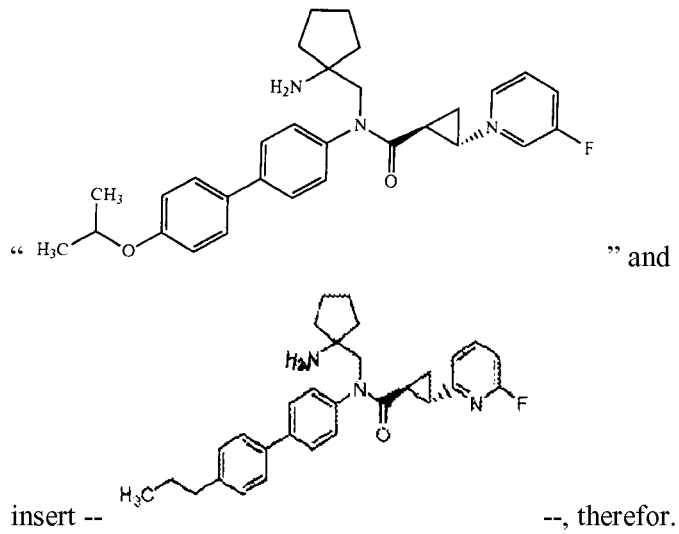

" and insert -- -- , therefor.

Signed and Sealed this
Fifth Day of November, 2013

Teresa Stanek Rea
*Deputy Director of the United States Patent and Trademark Office*

CERTIFICATE OF CORRECTION (continued)
U.S. Pat. No. 8,426,414 B2

In the Claims:

In Claim 2, col. 54, lines 17-25, delete

" 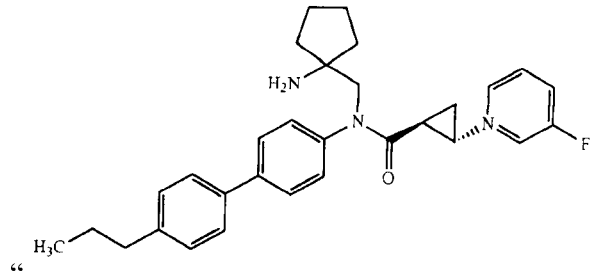 " and insert -- 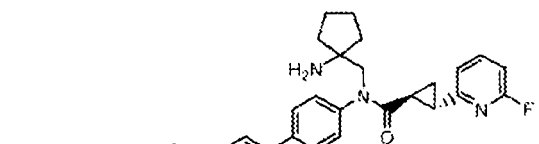 --, therefor.